(12) United States Patent
Ausen et al.

(10) Patent No.: US 7,185,401 B2
(45) Date of Patent: Mar. 6, 2007

(54) HEAT TREATED PROFILE EXTRUDED HOOK

(75) Inventors: Ronald W. Ausen, St. Paul, MN (US); William C. Unruh, Inver Grove Heights, MN (US); Philip Miller, Eagan, MN (US); Jayshree Seth, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 11/016,993

(22) Filed: Dec. 20, 2004

(65) Prior Publication Data

US 2005/0097713 A1 May 12, 2005

Related U.S. Application Data

(63) Continuation-in-part of application No. 10/411,042, filed on Apr. 10, 2003, now abandoned, which is a continuation-in-part of application No. 10/316,686, filed on Dec. 11, 2002, now abandoned, which is a continuation-in-part of application No. 10/214,051, filed on Aug. 7, 2002, now abandoned, which is a continuation-in-part of application No. 10/050,403, filed on Jan. 15, 2002, now abandoned.

(51) Int. Cl.
*A44B 18/00* (2006.01)

(52) U.S. Cl. .......................... 24/451; 24/442

(58) Field of Classification Search ............. 24/442, 24/450, 451, 452
See application file for complete search history.

(56) References Cited

U.S. PATENT DOCUMENTS

| 3,031,730 | A | 5/1962 | Morin |
|---|---|---|---|
| 3,138,841 | A | 6/1964 | Naimer |
| 3,214,816 | A | 11/1965 | Mathison |
| 3,266,133 | A | 8/1966 | Flanagan, Jr. |
| 3,557,407 | A | 1/1971 | Lemelson |

(Continued)

FOREIGN PATENT DOCUMENTS

EP 1 181 873 A1 2/2002

(Continued)

*Primary Examiner*—Jack W. Lavinder
(74) *Attorney, Agent, or Firm*—William J. Bond

(57) ABSTRACT

A method for forming a unitary polymeric projection or fastener comprising a thin, strong flexible backing, and a multiplicity of thin spaced hook members projecting from the upper surface of the unitary backing the method generally including extruding a thermoplastic resin through a die plate which die plate is shaped to form a base layer and spaced ridges, ribs or hook elements projecting above a surface of the base layer. When the die forms the spaced ridges or ribs the cross sectional shape of the hook members are formed by the die plate while the initial hook member thickness is formed by transversely cutting the ridges at spaced locations along their lengths to form discrete cut portions of the ridges. Subsequently longitudinal stretching of the backing layer (in the direction of the ridges on the machine direction) separates these cut portions of the ridges, which cut portion then form spaced apart hook members. The extruded hook members or cut rib hook members are then heat treated resulting in shrinkage of at least a portion of at least the hook head portion thickness by from 5 to 90 percent, preferably 30 to 90 percent.

50 Claims, 7 Drawing Sheets

U.S. PATENT DOCUMENTS

| | | | |
|---|---|---|---|
| 3,557,413 A | 1/1971 | Engle | |
| 3,632,716 A | 1/1972 | Fairbanks | |
| 3,682,760 A | 8/1972 | Fairbanks | |
| 3,694,537 A | 9/1972 | Fairbanks | |
| 3,808,646 A | 5/1974 | Brumlik | |
| 3,833,972 A | 9/1974 | Brumlik | |
| 3,840,945 A | 10/1974 | Brumlik | |
| 4,001,366 A | 1/1977 | Brumlik | |
| 4,056,593 A | 11/1977 | De Navas Albareda | |
| 4,076,656 A | 2/1978 | White et al. | |
| 4,189,809 A | 2/1980 | Sotos | |
| 4,290,174 A | 9/1981 | Kalleberg | |
| 4,454,183 A | 6/1984 | Wollman | |
| 4,894,060 A | 1/1990 | Nestegard | |
| 4,963,140 A | 10/1990 | Robertson et al. | |
| 5,077,870 A | 1/1992 | Melbye et al. | |
| 5,135,800 A | 8/1992 | Nagaoka | |
| 5,300,058 A | 4/1994 | Goulait | |
| 5,315,740 A | 5/1994 | Provost | |
| 5,325,569 A | 7/1994 | Goulait | |
| 5,326,612 A * | 7/1994 | Goulait | 428/100 |
| 5,537,723 A | 7/1996 | Yoshida et al. | |
| 5,604,963 A | 2/1997 | Akeno | |
| 5,616,394 A | 4/1997 | Gorman et al. | |
| 5,657,517 A | 8/1997 | Akeno | |
| 5,715,581 A | 2/1998 | Akeno | |
| 5,720,740 A | 2/1998 | Thomas | |
| 5,762,645 A | 6/1998 | Peck | |
| 5,792,408 A | 8/1998 | Akeno et al. | |
| 5,845,375 A | 12/1998 | Miller | |
| 5,879,604 A | 3/1999 | Melbye et al. | |
| 5,900,350 A * | 5/1999 | Provost et al. | 430/325 |
| 5,910,136 A | 6/1999 | Hetzler | |
| 5,913,482 A | 6/1999 | Akeno | |
| 5,928,212 A | 7/1999 | Kline et al. | |
| 5,933,927 A | 8/1999 | Miller et al. | |
| 5,997,981 A | 12/1999 | McCormack et al. | |
| 6,035,498 A | 3/2000 | Buzzell et al. | |
| 6,054,091 A | 4/2000 | Miller | |
| 6,096,014 A | 8/2000 | Haffner | |
| 6,209,177 B1 | 4/2001 | Murasaki | |
| 6,280,670 B1 | 8/2001 | Buzzell | |
| 6,303,062 B1 | 10/2001 | Aamodt et al. | |
| 6,357,088 B2 | 3/2002 | Provost | |
| 6,367,128 B1 | 4/2002 | Galkiewicz | |
| 6,478,784 B1 | 11/2002 | Johnson | |
| 6,484,371 B1 | 11/2002 | Romanko | |
| 6,623,469 B1 | 9/2003 | Thomas | |
| 6,708,378 B2 | 3/2004 | Parellada | |
| 6,766,918 B1 | 7/2004 | Bogdanovich | |
| 7,037,457 B2 | 5/2006 | Seidel | |
| 2002/0124359 A1 | 9/2002 | Muraski et al. | |
| 2002/0125605 A1 * | 9/2002 | Lacey et al. | 264/167 |
| 2002/0138064 A1 | 9/2002 | Appleton | |
| 2003/0106188 A1 | 6/2003 | Palafrugell | |
| 2003/0125706 A1 | 7/2003 | Hortonville | |
| 2003/0208302 A1 | 11/2003 | Lemelson | |

FOREIGN PATENT DOCUMENTS

| | | |
|---|---|---|
| JP | 63-167483 | 1/1990 |
| WO | WO 02/00793 | 1/2002 |
| WO | WO 02/060294 A1 | 8/2002 |
| WO | WO 02/067836 A2 | 9/2002 |
| WO | WO 02/069864 A2 | 9/2002 |

* cited by examiner

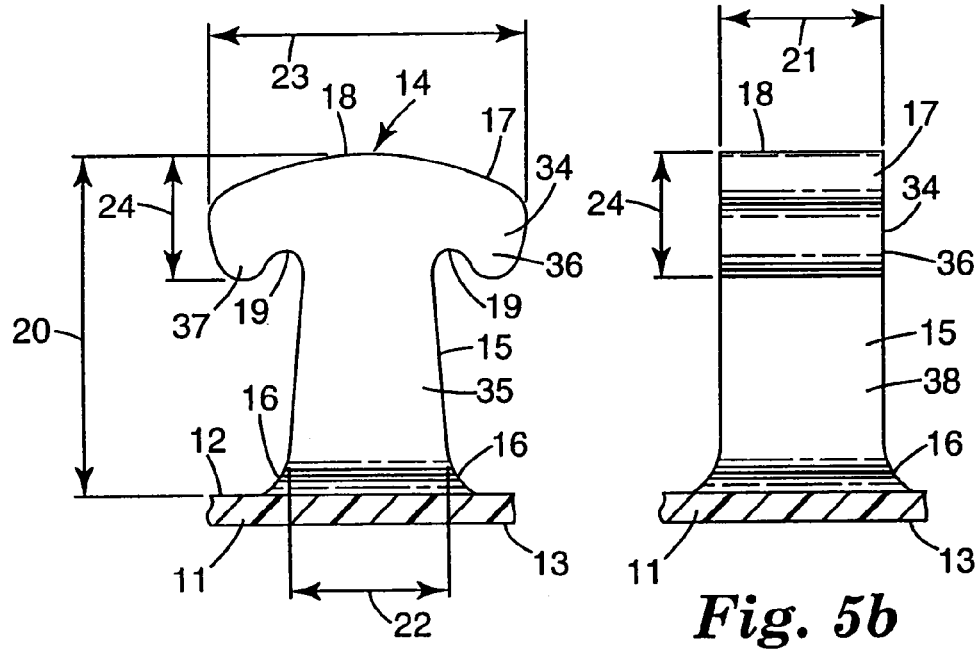
Fig. 5a
Fig. 5b
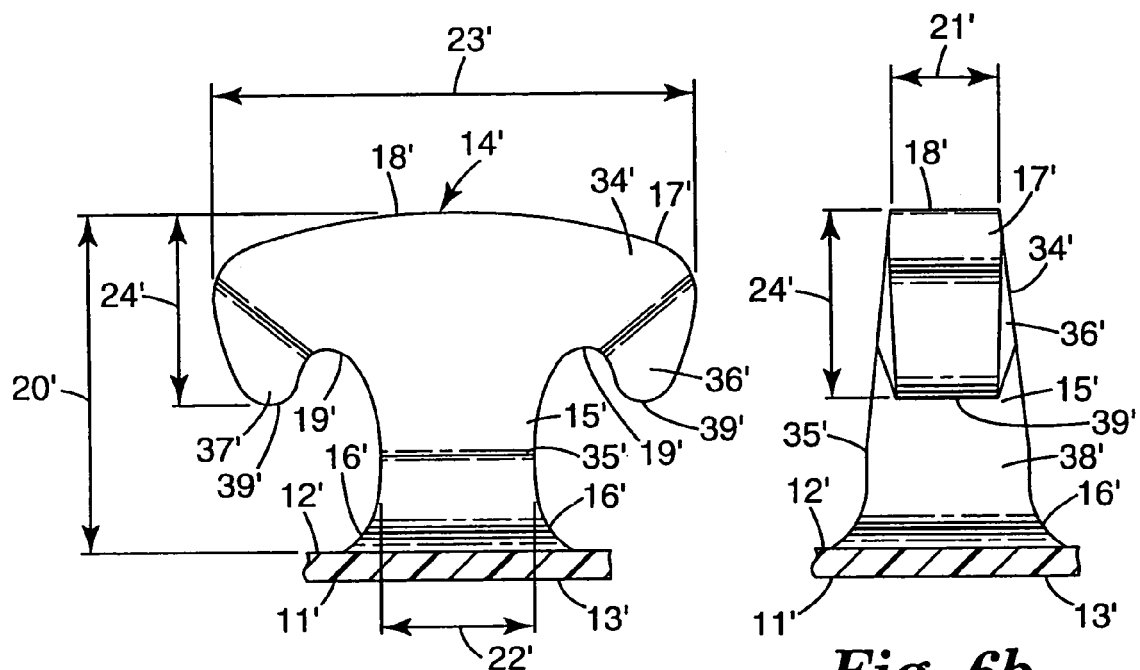
Fig. 6a
Fig. 6b

HEAT TREATED PROFILE EXTRUDED HOOK

CROSS REFERENCE TO RELATED APPLICATIONS

This application claims priority from application Ser. No 10/619,048, filed on Jul. 14, 2003, now U.S. Pat. No. 7,052,636, which is a continuation-in-part application of pending prior application Ser. No. 10/411,042, filed Apr. 10, 2003 now abandoned, which is a continuation-in-part of application Ser. No. 10/316,686, filed Dec. 11, 2002 (now abandoned), which is a continuation-in-part of application Ser. No. 10/214,051, filed Aug. 7, 2002 (now abandoned), which is a continuation-in-part of application Ser. No. 10/050,403, filed Jan. 15, 2002 (now abandoned).

BACKGROUND AND SUMMARY

The present invention concerns molded hook fasteners for use with hook and loop fasteners.

BACKGROUND OF THE INVENTION

There are a variety of methods known to form hook materials for hook and loop fasteners. One of the first manufacturing methods for forming hooks involved weaving loops of monofilaments into a fibrous or film backing or the like followed by cutting the filament loops to form hooks. These monofilament loops were also heated to form headed structures such as disclosed in U.S. Pat. Nos. 4,290,174; 3,138,841 or 4,454,183. These woven hooks are generally durable and work well for repeated uses. However, they are generally expensive and coarse to the touch.

For use in disposable garments and the like, it was generally desirable to provide hooks that were inexpensive and less abrasive. For these uses and the like, the solution was generally the use of continuous extrusion methods that simultaneously formed the backing and the hook elements, or precursors to the hook elements. With direct extrusion molding formation of the hook elements, see for example U.S. Pat. No. 5,315,740, the hook elements must continuously taper from the backing to the hook tip to allow the hook elements to be pulled from the molding surface. This generally inherently limits the individual hooks to those capable of engaging only in a single direction while also limiting the strength of the engaging head portion of the hook element.

An alternative direct molding process is proposed, for example, in U.S. Pat. No. 4,894,060, which permits the formation of hook elements without these limitations. Instead of the hook elements being formed as a negative of a cavity on a molding surface, the basic hook cross-section is formed by a profiled extrusion die. The die simultaneously extrudes the film backing and rib structures. The individual hook elements are then formed from the ribs by cutting the ribs transversely followed by stretching the extruded strip in the direction of the ribs. The backing elongates but the cut rib sections remain substantially unchanged. This causes the individual cut sections of the ribs to separate each from the other in the direction of elongation forming discrete hook elements. Alternatively, using this same type extrusion process, sections of the rib structures can be milled out to form discrete hook elements. With this profile extrusion, the basic hook cross section or profile is only limited by the die shape and hooks can be formed that extend in two directions and have hook head portions that need not taper to allow extraction from a molding surface. This is extremely advantageous in providing higher performing and more functionably versatile hook structures. However, a limitation with this method of manufacture is in forming hook structures that are extremely narrow in the extrusion direction of the ribs or the cut direction. Cutting the formed ribs at very closely spaced intervals is difficult at commercially acceptable production speeds. Further, when the cut length is extremely closely spaced the previously cut portions of the ribs tend to fuse due to the heat created by the cutting operation. As such, there is a need to improve this process so as to allow for production of narrower hook profiles and formation of the narrower hook profiles at commercially acceptable production speeds.

BRIEF DESCRIPTION OF THE INVENTION

The present invention provides a method for forming preferably a unitary polymeric hook fastener comprising a thin, strong flexible backing, and a multiplicity of thin, spaced hook members projecting from the upper surface of the unitary backing. The method of the invention generally can be used to form thin upstanding projections, which may or may not be hook members that project upwardly from the surface of a unitary film backing of at least a uniaxially oriented polymer. The hook members each comprise a stem portion attached at one end to the backing, and a head portion at the end of the stem portion opposite the backing. The head portion can also extend from a side of a stem portion or be omitted entirely to form alternative projections which can be other forms than a hook member. For hook members, the head portion preferably projects past the stem portion on at least one of two opposite sides. At least the hook head portions have been heat treated so as to decrease the hook head thickness and thereby reducing or eliminating molecular orientation in at least the hook head in the machine direction. Generally, the hook members suitable for use in the invention method, both before and after treatment, have a height dimension from the upper surface of the backing of less than 5000 µm. The stem and head portions generally have a thickness dimension of less than 1500 µm in a first direction parallel to the surfaces of the backing. The stem portions each have a width dimension in the range of 50 to 500 µm in a second direction, generally at a right angle to the first direction and parallel to the surfaces of the backing, and the head portions each have a width dimension in the second direction that is between 50 and 2000 µm greater than the width dimension of the stem portion and a total width of less than 5000 µm. There are generally at least 10, preferably 20 to 200 or 20 to 300 hook members per square centimeter of the base.

The fastener is preferably made by a novel adaptation of a known method of making hook fasteners as described, for example, in U.S. Pat. Nos. 3,266,113; 3,557,413; 4,001,366; 4,056,593; 4,189,809 and 4,894,060 or alternatively U.S. Pat. No. 6,209,177, the substance of which are incorporated by reference in their entirety. The preferred method generally includes extruding a thermoplastic resin through a die plate which die plate is shaped to form a base layer and spaced ridges, ribs or hook elements projecting above a surface of the base layer. These ridges generally form the cross-section shapes of the desired projection to be produced, which is preferably a hook member. When the die forms the spaced ridges or ribs the cross sectional shape of the hook members are formed by the die plate while the initial hook member thickness is formed by transversely cutting the ridges at spaced locations along their lengths to form discrete cut portions of the ridges. Subsequently longitudinal stretching of the backing layer (in the direction of the ridges on the machine direction) separates these cut portions of the ridges, which cut portion then form spaced apart hook members. The extruded hook members or cut rib hook members are then heat treated resulting in shrinkage of at least a portion of at least the hook head portion thickness by from 5 to 90 percent, preferably 30 to 90 percent. In an alternative embodiment, the heat treatment is continued to likewise shrink at least a portion of the stem portion of the hook members. The resulting heat treated projections, preferably hooks, are substantially upstanding or rigid such that they do not droop toward the base layer or are able to penetrate a fibrous or like substrate. In a particular preferred embodiment, the extruded thermoplastic resin contains an immiscible phase to increase the extent of molecular orientation in the thermoplastic polymer or increase the degree of hook member or projection shrinkage when heat treated.

BRIEF DESCRIPTION OF THE DRAWINGS

The present invention will be further described with reference to the accompanying drawings wherein like reference numerals refer to like parts in the several views, and wherein:

FIGS. 5a and 5b are enlarged fragmentary side and end views, respectively, of one hook member in the hook fastener portion of FIG. 4.

FIGS. 6a and 6b are views of FIGS. 5a and 5b, respectively, after limited heat treating of the hook member.

DETAILED DESCRIPTION OF THE PREFERRED EMBODIMENT

Figure 4:
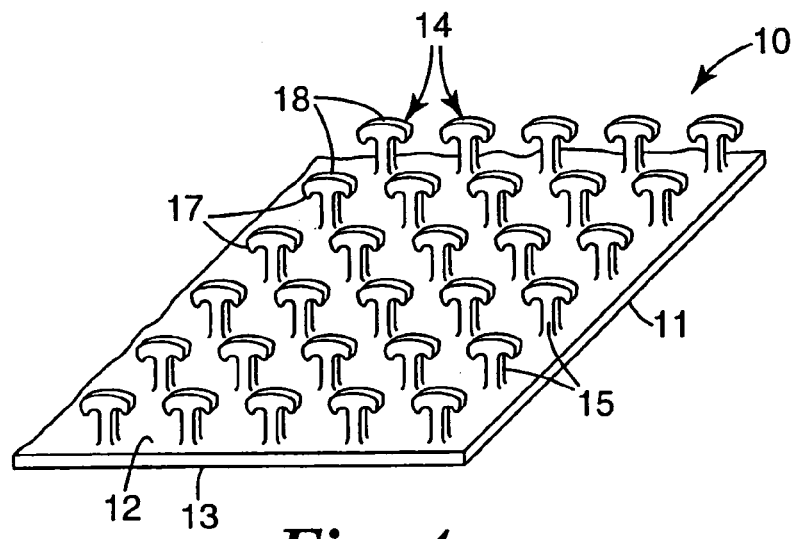
FIG. 4 is an enlarged perspective view of a hook fastener.

Referring now to FIG. 4 is an exemplary polymeric hook fastener portion, which can be produced, or heat treated according to the present invention is generally designated by the reference numeral 10. The hook fastener portion 10 comprises a thin strong flexible film-like backing 11 having generally parallel upper and lower major surfaces 12 and 13, and a multiplicity of spaced hook members 14 projecting from at least the upper surface 12 of the backing 11. The backing can have planar surfaces or surface features as could be desired for tear resistance or reinforcement. As is best seen in FIG. 5, the hook members 14 each comprise a stem portion 15 attached at one end to the backing 11 and preferably having tapered sections 16 that widen toward the backing 11 to increase the hook anchorage and breaking strengths at their junctures with the backing 11, and a head portion 17 at the end of the stem portion 15 opposite the backing 11. The sides 34 of the head portion 17 can be flush with the sides 35 of the stem portion 15 on two opposite sides. The head portion 17 has hook engaging parts or arms 36, 37 projecting past the stem portion 15 on one or both sides 38. The hook member shown in FIGS. 5a and 5b has a rounded surface 18 opposite the stem portion 15 to help the head portion 17 enter between loops in a loop fastener portion. The head portion 17 also has transverse cylindrically concave surface portions 19 at the junctures between the stem portion 15 and the surfaces of the head portion 17 projecting over the backing 11.

With reference to FIGS. 5a and 5b, there is shown a single representative one of the small hook members 14 on which its dimensions are represented by reference numerals between dimensional arrows. The height dimension is 20. The stem and head portions 15 and 17 have a thickness dimension 21, which as shown is the same, and the head portions 17 have a width dimension 23 and an arm droop 24. The stem portion has a width dimension 22 at its base before flaring 16 to the base film 11. The thickness as shown is for a rectilinear shaped hook, with other shapes the thickness can be measured as the shortest distance between two opposing sides 34 or 35. Likewise, the width dimension can be measured as the shortest distance between two opposing sides.

Figure 8:
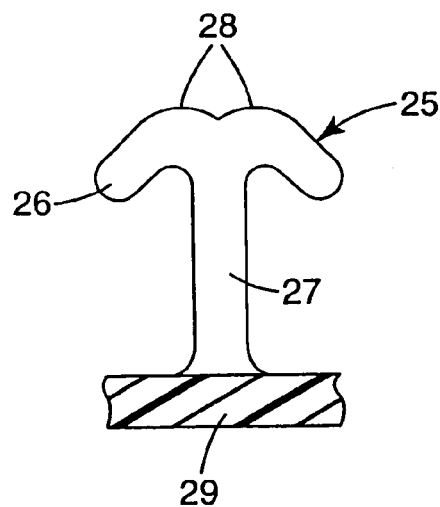
FIGS. 8 and 9 are enlarged fragmentary sectional views of alternate embodiments of hook portions that can be used in hook fastener portions according to the present invention.
Figure 9:
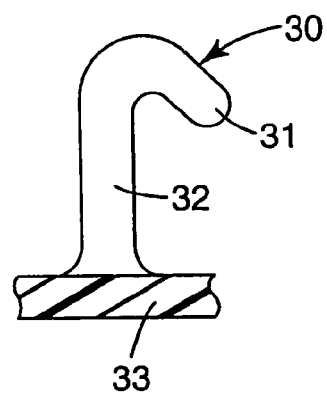

FIGS. 8 and 9 illustrate two of many alternate shapes that could be used for the hook members in alternate embodiments of the hook members that can be heat treated in accordance with the invention method.

The hook member 25 illustrated in FIG. 8 differs from the hook member 14 of FIG. 5 in that its head portion 26 projects farther on opposite sides from its stem portion 27 and is generally uniformly thick so that it can more easily bend to engage with or disengage from loops on a loop fastener portion.

The hook member 30 illustrated in FIG. 9 differs from the hook member 14 of FIG. 5 in that its head portion 31 projects from only one side of its stem portion 32 and will thus cause significantly greater peel forces when peeled away from the direction the head portion 31 projects than when it is peeled toward the direction the head portion 31 projects.

Figure 1:
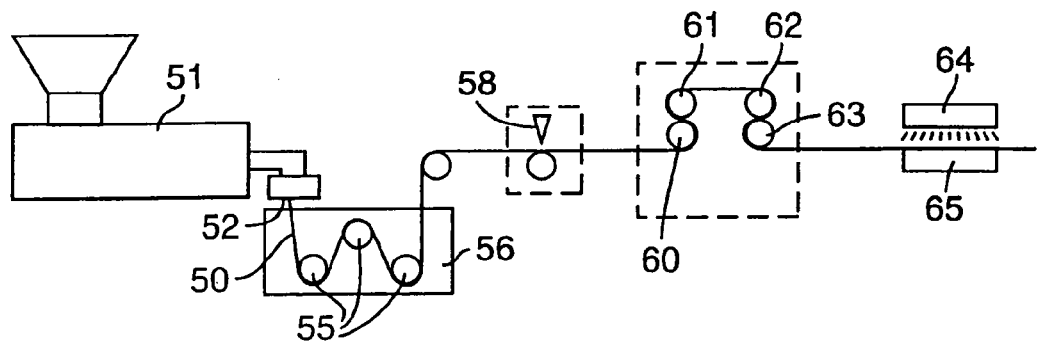
FIG. 1 schematically illustrates a method for making the hook fastener portion of FIG. 4.
Figure 2:
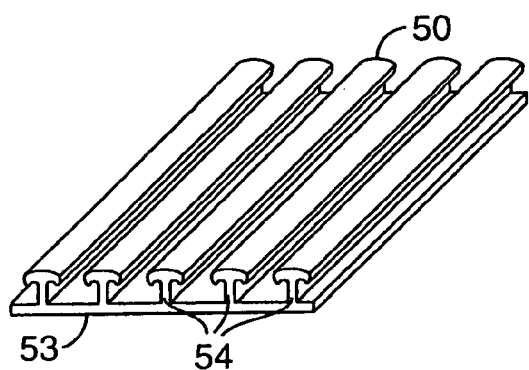
FIGS. 2 and 3 illustrate the structure of a strip at various stages of its processing in the method illustrated in FIG. 1.
Figure 3:
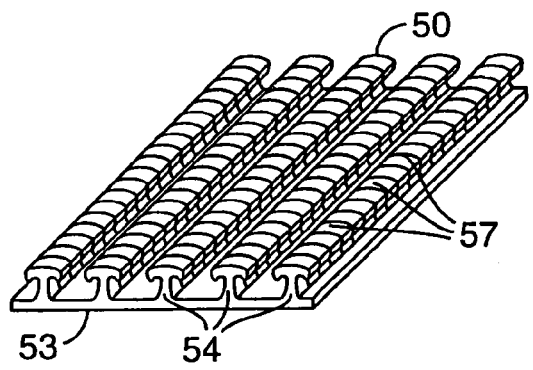

A first embodiment method for forming a hook fastener portion, such as that of FIG. 4, is schematically illustrated in FIG. 1. Generally, the method includes first extruding a strip 50 shown in FIG. 2 of thermoplastic resin from an extruder 51 through a die 52 having an opening cut, for example, by electron discharge machining, shaped to form the strip 50 with a base 53 and elongate spaced ribs 54 projecting above an upper surface of the base layer 53 that have the cross sectional shape of the hook portions or members to be formed. The strip 50 is pulled around rollers 55 through a quench tank 56 filled with a cooling liquid (e.g., water), after which the ribs 54 (but not the base layer 53) are transversely slit or cut at spaced locations along their lengths by a cutter 58 to form discrete portions 57 of the ribs 54 having lengths corresponding to about the desired thicknesses of the hook portions to be formed, as is shown in FIG. 3. The cut can be at any desired angle, generally from 90° to 30° from the lengthwise extension of the ribs. Optionally, the strip can be stretched prior to cutting to provide further molecular orientation to the polymers forming the ribs and/or reduce the size of the ribs and the resulting hook members formed by slitting of the ribs. The cutter 58 can cut using any conventional means such as reciprocating or rotating blades, lasers, or water jets, however preferably it cuts using blades oriented at an angle of about 60 to 80 degrees with respect to lengthwise extension of the ribs 54.

After cutting of the ribs 54, the base 53 of the strip 50 is longitudinally stretched at a stretch ratio of at least 2 to 1, and preferably at a stretch ratio of about 4 to 1, preferably between a first pair of nip rollers 60 and 61 and a second pair of nip rollers 62 and 63 driven at different surface speeds. Optionally, the strip 50 can also be transversely stretched to provide biaxial orientation to the base 53. Roller 61 is preferably heated to heat the base 53 prior to stretching, and the roller 62 is preferably chilled to stabilize the stretched base 53. Stretching causes spaces between the cut portions 57 of the ribs 54, which then become the hook portions or members 14 for the completed hook fastener portion 10. The formed hook members are then heat treated preferably by a non-contact heat source 64. The temperature and duration of the heating should be selected to cause shrinkage or thickness reduction of at least the head portion by from 5 to 90 percent. The heating is preferably accomplished using a non-contact heating source which can include radiant, hot air, flame, UV, microwave, ultrasonics or focused IR heat lamps. This heat treating can be over the entire strip containing the formed hook portions or can be over only a portion or zone of the strip. Or different portions of the strip can be heat treated to more or less degrees of treatment. In this manner, it is possible to obtain on a single strip hook containing areas with different levels of performance without the need to extrude different shaped rib profiles. This heat treatment can change hook elements continuously or in gradients across a region of the hook strip. In this manner, the hook elements can differ continuously across a defined area of the hook member. Further, the hook density can be the same in the different regions coupled with substantially the same film backing caliper or thickness (e.g., 50 to 500 microns). The caliper can easily be made the same as the hook strip will have the same basis weight and same relative amount of material forming the hook elements and backing in all regions despite the difference in the shape of the hooks caused by the subsequent heat treating. The differential heat treatment can be along different rows or can cut across different rows, so that different types of hooks, such as hooks having different hook thicknesses, can be obtained in a single or multiple rows in the machine direction or the lengthwise direction of the hook strip. The heat treatment can be performed at any time following creation of the hook element, such that customized performance can be created without the need for modifying the basic hook element manufacturing process.

FIG. 6 shows a hook member of the FIG. 5 hook after it has been heat treated to cause a reduction in the thickness 21' of the hook head portion 17'. The other dimensions of the hook member can also change which is generally as a result of conservation of mass. The height 20' generally increases a slight amount and the head portion width 23' increases as does the arm droop 24'. The stem and head portions now have a thickness dimension 21' that is nonuniform and tapers from the base to the head portion due to the incomplete heat treatment along the entire hook member 14'. Generally the untreated portion has a uniform thickness corresponding to the original thickness 21, the generally fully heat treated portion will have a uniform thickness 21' with a transition zone separating the untreated and treated portions. In this embodiment, the incomplete heat treatment also results in variation of the thickness 21' of the hook head portion from the arm tip to the arm portion adjacent the stem 15'. All other numbered elements in FIGS. 6a and 6b correspond to the numbered elements of FIGS. 5a and 5b.

Reduction in the hook member thickness is caused by relaxation of at least the melt flow induced molecular orientation of the hook head and/or stem portion which is in the machine direction, which generally corresponds to the thickness direction. Also, further reduction in thickness can occur where there is stretch induced molecular orientation, as where the ribs are stretched longitudinally prior to cutting. Melt induced molecular orientation is created by the melt extrusion process as polymer, under pressure and shear forces, is forced through the die orifice(s). The rib or ridge forming sections of the die create the molecular orientation in the formed ribs. This molecular orientation extends longitudinally or in the machine direction along the ribs or ridges. When the ribs or ridges are cut, the molecular orientation extends generally in the thickness dimension of the cut ribs, or cut hook members, however, the molecular orientation can extend at an angle of from about 0 to 45 degrees to the hook member thickness. The initial molecular orientation in the hook members is generally at least 10 percent, preferably 20 to 100 percent (as defined below). When the hook members are heat treated in accordance with the invention, the molecular orientation of the hook members decrease and the hook member thickness dimension decreases. The amount of thickness reduction depends primarily on the amount of hook member molecular orientation extending in the machine direction or hook thickness dimension. The heat treatment conditions, such as time of treatment, temperature, the nature of the heat source and the like can also effect the hook member thickness reduction. As the heat treatment progresses, the reduction in hook member, or projection thickness extends from the hook head portion, or top of the projection, to the stem portion, or down the projection to the base, until the entire hook member thickness has been reduced. Generally, the thickness reduction is substantially the same in the stem and the hook head portions when both are fully heat treated or partially heat treated to the same extent. When only a part of the hook head portion and/or hook head portion and stem portion are heat treated, there is a transition zone where the thickness increases from the upper heat treated portion, generally the head portion, to the substantially non-heat treated portion of the stem portion, or stem portion and part of the hook head portion, which have a substantially unreduced thickness. When the thickness dimension shrinks, the width of the treated portion generally increases, while the overall hook member height increases slightly and the arm droop increases. The end result is a hook thickness that can either, not be economically produced directly, or cannot be produced at all by conventional methods. The heat treated projection, generally the hook head, and optionally stem, is also characterized by a molecular orientation level of less than 10 percent, preferably less than 5 percent where the base film layer orientation is substantially unreduced. Generally, the hook member stem or projection orientation immediately adjacent the base film layer will be 10 percent or higher, preferably 20 percent or higher.

FIG. 7 is a schematic view of a hook member of the FIG. 5 hook, where the entire hook member has been subjected to heat treatment. In this case, both the hook head portion 17" and the stem portion 15" have shrunk in the thickness direction with corresponding increases in the width dimensions 23" and 22" and arm droop 24". In this case, both the stem and head portion have a generally uniform thickness dimension 21", which is less than the initial hook member width dimension 21. The tapered section 16" is generally larger than the initial tapered section 16 due to the thickness reduction in the stem portion.

The heat treatment is generally carried out at a temperature near or above the polymer melt temperature. As the heat gets significantly above the polymer melt temperature, the treatment time decreases so as to minimize any actual melting of the polymer in the hook head portion or top of the projection. The heat treatment is carried out at a time sufficient to result in reduction of the thickness of the hook head, and/or stem, but not such that there is a significant deformation of the backing or melt flow of the hook head portion or top of the projection. Heat treatment can also result in rounding of the hook head portion edges, improving tactile feel for use in garment applications.

Unexpectedly it has been discovered, that for high performance microhook engagement with certain low cost or low loft loop fabrics, that this heat treatment substantially increases engagement of the microhooks to the loop fabrics. A particularly preferred novel, microhook member producible by the invention method has been discovered where the hook members have a height of less than 1000 µm, preferably from 300 to 800 µm, and at least a head portion with a thickness of from 50 to 200 µm, preferably 50 to 180 µm. The other dimensions for this improved microhook include a stem width, as defined above, of from 50 to 500 µm, a head portion width of from 100 to 800 µm, and an arm droop of from 50 to 700 µm, preferably 100 to 500 µm, and a hook density of at least 50 and preferably from about 70 to 150, up to 300, hooks per square centimeter. This novel microhook hook portion exhibits improved overall performance to a variety of low loft loop fabrics.

Figure 15:
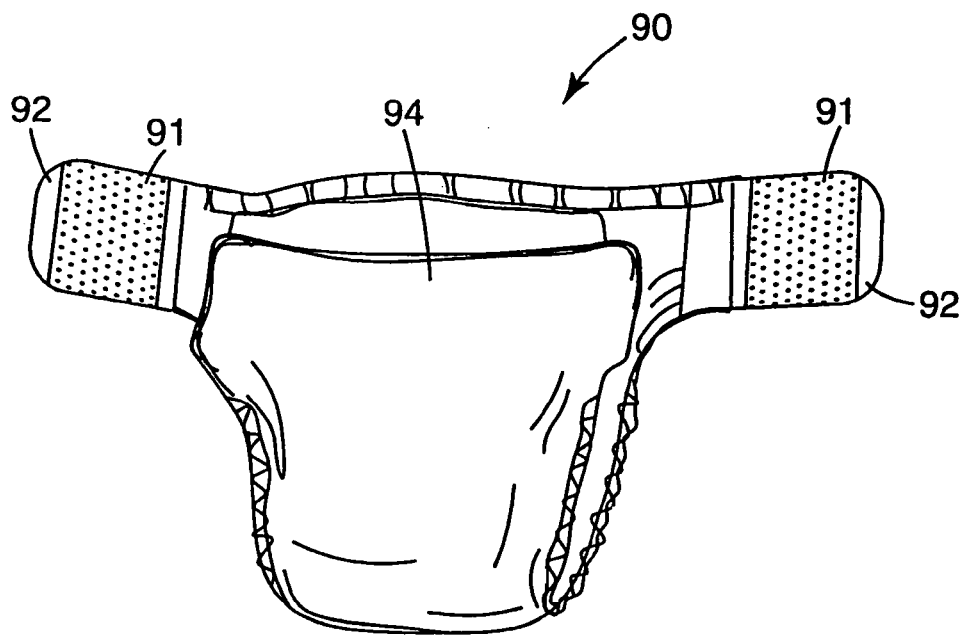
FIG. 15 is a perspective view of a disposable garment using a preferred hook member according to the present invention.
Figure 16:
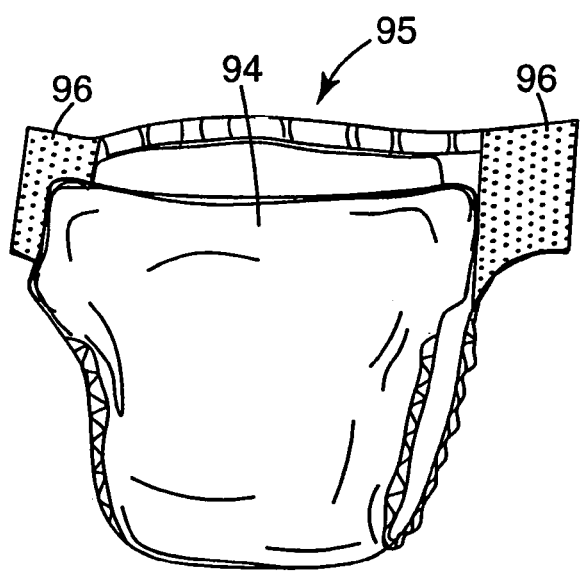
FIG. 16 is a perspective view of a disposable garment using a preferred hook member according to the present invention.
Figure 17:
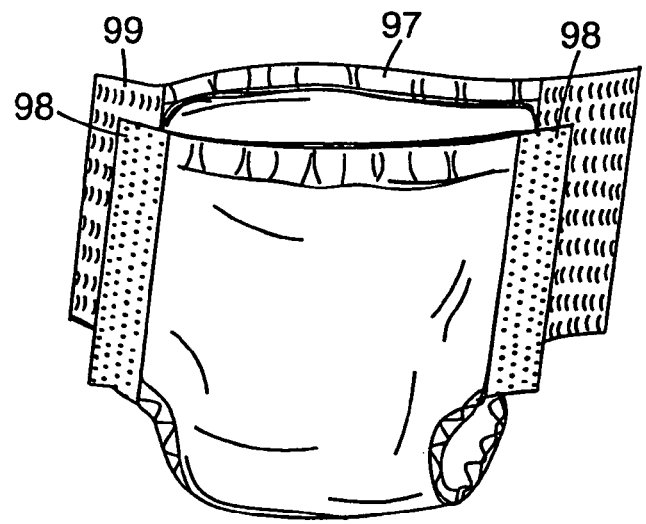
FIG. 17 is a perspective view of a disposable garment using a preferred hook member according to the present invention.
Figure 18:
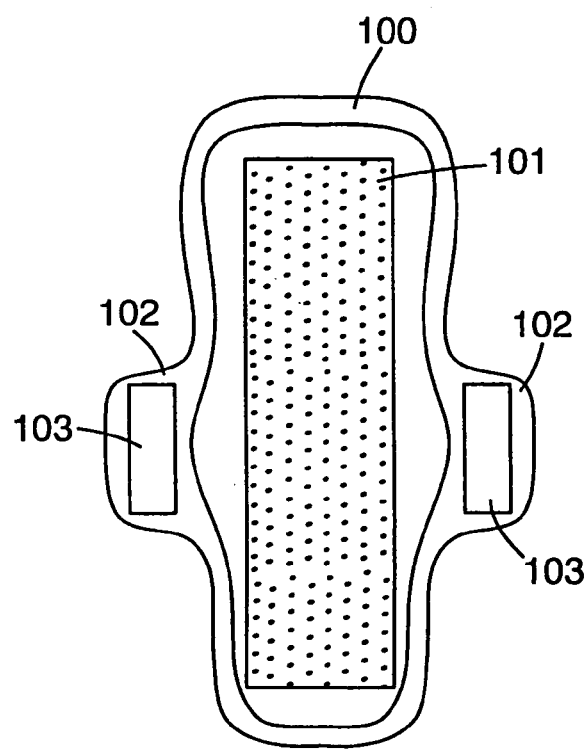
FIG. 18 is a perspective view of a feminine hygiene article.

In certain applications, it has unexpectedly been discovered that very low hook densities are desirable. For example, hook densities of less than 100, preferably less than 70 and even less than 50 hook per square centimeter are desirable when used to attach to low loft nonwovens using a relatively large area flexible hook tab or patch. This low spacing has been found to increase the hooking efficiency of the individual hook element, particularly relative to low cost and otherwise ineffective nonwoven materials not traditionally used as loop products. The hook tab or patch can be made flexible by suitable selection of the polymer forming the base layer and/or by stretching the base layer at an angle transverse to the longitudinal stretching. This transverse stretching creates biaxial orientation in the base layer reducing its thickness, for example from 20 µm to 100 µm, preferably 30 µm to 60 µm. Biaxial orientation also reduces the hook density to the desired range for low density hook application. Examples of suitable uses for this low density hook element, as a tab or patch, are illustrated in FIGS. 15–18. In FIG. 15, a large area fastening tab is attached to a carrier substrate 92, which is attached to a diaper 90 as is known in the art. The fastening tab could be of a size of from 5 to 100 cm$^2$, preferably 20 to 70 cm$^2$ and can be attached directly to a low loft nonwoven 95 forming the outer cover of the diaper. Typically, this low loft nonwoven would be a spunbond web, a bonded carded or air laid web, a spunlace web or the like. FIG. 16 is a variation of this fastening tab type construction for a diaper 95, however, where the hook tab 96 is directly bonded to the diaper 95, either at an ear cutout portion or at the edge region of the diaper. FIG. 17 is a further embodiment of a large area hook tab 98 used with a pull up type diaper design. In this embodiment, the hook tab 98 would engage a suitable mating region 99 on the opposite face of the pull up diaper. Of course, these two elements could be reversed. In both cases, the mating region could be a nonwoven used to form the nonwoven outer cover of the diaper or the nonwoven fluid permeable topsheet. FIG. 18 is an embodiment of the invention hook material being used as a large area patch 101 on a feminine hygiene article 100. The patch could be used as the primary attachment element to the undergarment, optionally a secondary attachment element 103 could be provided on attachment wings 102. The use of the low density hook element as a large area patch could also be used on a diaper where the patch could form a part or all of the diaper outer cover.

Suitable polymeric materials from which the hook fastener portion can be made include thermoplastic resins comprising polyolefins, e.g. polypropylene and polyethylene, polyvinyl chloride, polystyrene, nylons, polyester such as polyethylene terephthalate and the like and copolymers and blends thereof. Preferably the resin is a polypropylene, polyethylene, polypropylene-polyethylene copolymer or blends thereof.

In a preferred embodiment, the orientable thermoplastic resin is blended with a material that will form a distinct second phase. The orientable thermoplastic resin constitutes a continuous first phase, generally 50 percent or greater by volume of the volume of the blend as extruded. The thermoplastic resin can be a single resin or a homogeneous or a mechanically compatible blend. Compatibility of polymer blends can be determined by using differential scanning calorimetry (DSC) to measure the melting points and glass transition temperatures of the polymer blend. If two glass transition temperatures are detected by DSC due to the constituent polymers in the blend, the blend is said to be incompatible. If a single glass transition temperature, intermediate between those of the component polymers, is detected, the blend is said to be compatible. Mechanically compatible blends represent a deviation from this generality, since they exhibit two glass transition temperatures but have finer morphology, are translucent and are extrudable without gross phase separation. Such blends are useful in this invention. The distinct second phase is generally a discontinuous phase but also could be a continuous phase. The presence of a distinct second phase results in substantial increases in the degree of heat shrinkage of the heat treated projection or hook. The distinct second phase could preferably be a gas, a nonparticulate diluent, a phase distinct thermoplastic polymer, a tackifier or combination of these materials.

Examples of preferred nonparticulate diluents that can be used in combination with the thermoplastic resins include, but are not limited to, mineral oils, petroleum jelly, low molecular weight polyethylene, soft Carbowax and mixtures thereof. Mineral oils are preferred among these diluents because of their relatively low cost. The diluents may optionally be partially or entirely extracted from the extruded hook film by known methods. The diluents can be varied within a wide range within the starting thermoplastic resin used for production of the film backed fastener. The amount of diluents used is preferably in the range of 20–60% by weight, and more preferably 25–40% by weight of the starting thermoplastic material. If the amount of diluent added to the starting material is under 20% by weight, the increase in shrinkage of the hook element or projection is reduced, while if it is above 60% by weight it becomes more difficult to produce flexible coherent film backed fasteners.

Physical or chemical blowing agents are useful in the present invention to form distinct gas phases. A blowing agent may be any material that is capable of forming a vapor at the temperature and pressure at which the extrudate exits the die. A blowing agent may be a physical blowing agent. A physical blowing agent may be introduced, i.e., injected into the thermoplastic material as a gas or supercritical fluid. Flammable blowing agents such as pentane, butane and other organic materials may be used, but non-flammable, non-toxic, non-ozone depleting blowing agents such as carbon dioxide, nitrogen, water, $SF_6$, nitrous oxide, argon, helium, noble gases, such as xenon, air (nitrogen and oxygen blend), and blends of these materials are preferred because they are easier to use, e.g., fewer environmental and safety concerns. Other suitable physical blowing agents include, e.g., hydrofluorocarbons (HFC), hydrochlorofluorocarbons (HCFC), and fully- or partially fluorinated ethers.

If chemical blowing agents are used, they are preferably added to the thermoplastic resin at a temperature below that of the activation temperature of the blowing agent, and are typically added to the thermoplastic resin feed at room temperature prior to introduction to the extruder. The blowing agent is then mixed to distribute it throughout the polymer in unactivated form, above the melt temperature of the thermoplastic resin, but below the activation temperature of the chemical blowing agent. Once dispersed, the chemical blowing agent may be activated by heating the mixture to a temperature above the activation temperature of the agent. Activation of the blowing agent liberates gas either through decomposition (e.g., exothermic chemical blowing agents such as azodicarbonamide) or reaction (e.g., endothermic chemical blowing agents such as sodium bicarbonate-citric acid mixtures), such as $N_2$, $CO_2$ and/or $H_2O$, yet cell formation is restrained by the temperature and pressure of the system. Useful chemical blowing agents typically activate at a temperature of 140° C. or above.

Examples of chemical blowing agents include synthetic azo-, carbonate-, and hydrazide based molecules, including azodicarbonamide, azodiisobutyronitrile, benzenesulfonhydrazide, 4,4-oxybenzene sulfonyl-semicarbazide, p-toluene sulfonyl semi-carbazide, barium azodicarboxylate, N,N'-dimethyl-N,N'-dinitrosoterephthalamide and trihydrazino triazine. Specific examples of these materials are Celogen OT (4,4'oxybis(benzenesulfonylhydrazide)). Other chemical blowing agents include endothermic reactive materials such as sodium bicarbonate/citric acid bends that release carbon dioxide. Specific examples include Reedy International Corp SAFOAM products.

When the extrudate exit temperature is at or below 50° C. above the $T_m$ of the thermoplastic resin, the increase in $T_m$ of the resin as the blowing agent comes out of the solution causes crystallization of the thermoplastic resin, which in turn arrests the growth and coalescence of the foam cells. When exit temperatures are in excess of 50° C. above the $T_m$ of the thermoplastic resin, cooling of the resin may take longer, resulting in non-uniform, unarrested cell growth.

The amount of blowing agent incorporated into the foamable thermoplastic phase is generally chosen to yield a foam having a void content in excess of 10%, more preferably in excess of 20%, as measured by density reduction; [1−the ratio of the density of the foam to that of the neat polymer]× 100.

Preferably, the formed foam is oriented such as by uniaxial or biaxial stretching in mutually perpendicular directions at a temperature above the alpha transition temperature and below the melting temperature of the thermoplastic phase. Foams may be stretched in one or both directions 3 to 50 times total draw ratio (MD×CD) for biaxial stretching or 1–10 times for uniaxial stretching. Generally greater orientation is achievable using foams of small cell size; foams having cell size of greater than 100 microns are not readily biaxially oriented more than 20 times (MD×CD), while foams having a cell size of 50 microns or less could be stretched up to 50 times total draw ratio. In addition foams with small average cell size exhibit greater tensile strength and elongation to break after stretching. Small cell sizes (100 microns or less) in combination with the orientation allows a foam sheet thickness of 25 microns to 1000 microns, and foam sheets of 25 microns to 100 microns are readily prepared. This is extremely desirable with hook structures, as a soft conformable backing is obtained that can be used in many uses where contact with an active wearer (e.g., a person) is desired or possible. Specifically, the foamed hook can be used with disposable absorbent articles such as diapers as a closure tab, which is soft to the touch and is aesthetically pleasing due to its pearlescent appearance. Other uses where a hook strip or tab would be in contact with a sensitive surface would include medical wrap, sport wraps, headbands, produce wraps and feminine hygiene articles. Suitable backings can have a stiffness of from 10 to 2000 Gurley stiffness units, preferably from 10 to 200 Gurley stiffness units.

Preferably, the foam can have cell sizes of 2 to 100 microns, preferably 5 to 50 microns. The foam may alternatively, or additionally, have a cell size distribution with a polydispersity from 1.0 to 2.0, preferably from 1.0 to 1.5, more preferably from 1.0 to 1.2.

For forming these foams, the thermoplastic orientable resins are preferably high melt strength polyolefins, such as branched polyolefins. These high melt strength polymers help control the growth of the foam cells within the desired range necessary for creating the discrete microstructures and prevent collapse of the cells during surface microstructure formation if needed. Suitable semi-crystalline materials include polyethylene, polypropylene, polymethylpentene, polyisobutylene, polyolefin copolymers, Nylon 6, Nylon 66, polyester, polyester copolymers, fluoropolymers, poly vinyl acetate, poly vinyl alcohol, poly ethylene oxide, functionalized polyolefins, ethylene vinyl acetate copolymers, metal neutralized polyolefin ionomers available under the trade designation SURLYN (E.I. DuPont de Nemours, Wilmington, Del.), polyvinylidene fluoride, polytetrafluoroethylene, polyformaldehyde, polyvinyl butyral, and copolymers having at least one semi-crystalline compound. Preferred high melt strength polymers are high melt strength polypropylenes which include homo- and copolymers containing 50 weight percent or more propylene monomer units, preferably at least 70 weight percent, and have a melt strength in the range of 25 to 60 cN at 190° C. Melt strength may be conveniently measured using an extensional rheometer by extruding the polymer through a 2.1 mm diameter capillary having a length of 41.9 mm at 190° C. and at a rate of 0.030 cc/sec; the strand is then stretched at a constant rate while measuring the force to stretch at a particular elongation. Preferably the melt strength of the polypropylene is in the range of 30 to 55 cN, as described in WO 99/61520.

Such high melt strength polypropylenes may be prepared by methods generally known in the art. Reference may be made to U.S. Pat. No. 4,916,198 which describes a high melt strength polypropylene having a chain-hardening elongational viscosity prepared by irradiation of linear propylene in a controlled oxygen environment. Other useful methods include those in which compounds are added to the molten polypropylene to introduce branching and/or crosslinking such as those methods described in U.S. Pat. No. 4,714,716, WO 99/36466 and WO 00/00520. High melt strength polypropylene may also be prepared by irradiation of the resin as described in U.S. Pat. No. 5,605,936. Still other useful methods include forming a bipolar molecular weight distribution as described in J I Raukola, "A New Technology To Manufacture Polypropylene Foam Sheet And Biaxial Oriented Foam Film", VTT Publications 361, Technical Research Center of Finland, 1998 and in U.S. Pat. No. 4,940,736.

A second distinct phase can be formed by a blend of two or more incompatible thermoplastic polymers. Compatibility can be determined by using differential scanning calorimetry (DSC) to measure the melting points and glass transition temperatures of the polymer blend. If two glass transition temperatures are detected by DSC due to the constituent polymers in a blend, the blend is said to be incompatible. If a single glass transition temperature, intermediate between those of the component polymers, is detected, the blend is said to be compatible. Phase distinct polymer blends can be prepared from blends of olefinic polymers with non-olefinic polymers. Examples of olefinic polymers include polypropylene, polyethylene, propylene-ethylene random and impact copolymers, polybutenes and polyethylenevinylacetates. Examples of non-olefinic polymers include polystyrenes, polyamides, polyurethanes and polyesters. Block copolymers such as styrene-isoprene-styrene (SIS) and styrene-ethylenebutylene-styrene (SEBS) are useful as one of the constituents of the blends.

The backing of the fastener must be thick enough to allow it to be attached to a substrate by a desired means such as sonic welding, heat bonding, sewing or adhesives, including pressure sensitive or hot melt adhesives, and to firmly anchor the stems and provide resistance to tearing when the fastener is peeled open. However, when a fastener is used on a disposable garment, the backing should not be so thick that it is stiffer than necessary. Generally, the backing has a Gurley stiffness of 10 to 2000, preferably 10 to 200 so as to allow it to be perceived as soft when used either by itself or laminated to a further carrier backing structure such as a nonwoven, woven or film-type backing, which carrier backing should also be similarly soft for use in disposable absorbent articles. The optimum backing thickness will vary depending upon the resin from which the hook fastener portion is made, but will generally be between 20 μm and 1000 μm, and is preferably 20 to 200 μm for softer backings.

Figure 10:
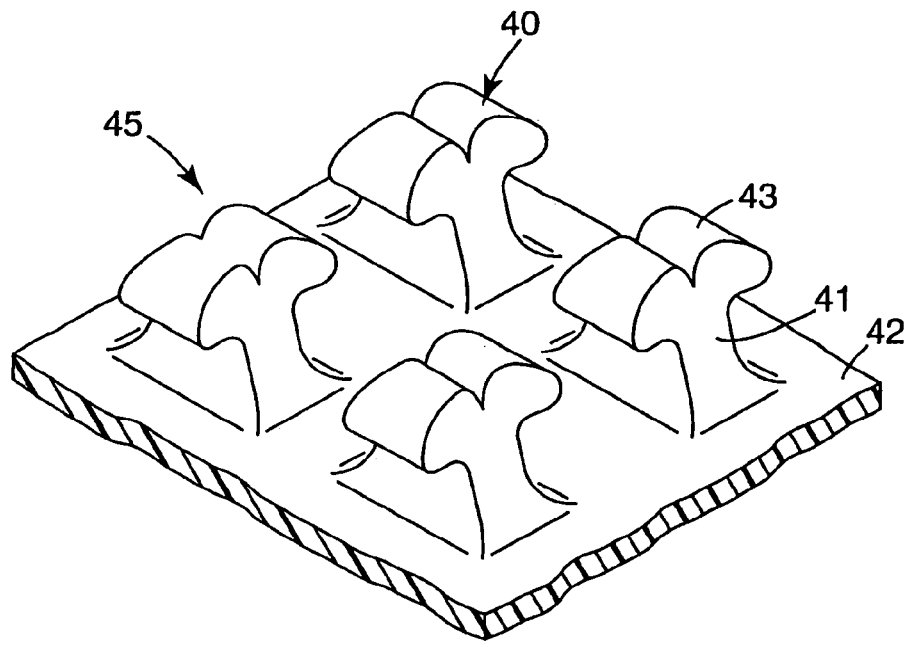
FIG. 10 is an alternative embodiment of individual extruded hook elements that can be heat treated in accordance with the invention method.

An alternative method for extruding hook members from a die is described in U.S. Pat. No. 6,209,177 which results in hook fastening portions such as shown in FIG. 10. Each of the hook members comprises a stem portion 41 projecting from the surface of the backing 42 and a hook head 43 projecting from an end of the stem portion 41 sideways in at least one direction. A thickness of the hook member 40, which is perpendicular to a projecting direction of the hook head portion 43 of the hook member 40, gradually increases from a top portion of the hook head portion 43 toward a rising base end of the stem portion 41. With these hook members 40 each hook member 40 is molded independently of each other and integral with the surface of the backing substrate 42, in contrast to cutting of ribs and drawing of the backing substrate. The molten resin is extruded through a die plate however in this method a face of the die includes an ascending/descending member vertically reciprocating in sliding contact with a front of the die face interrupting polymer flow to the die elements forming the ridges. During extrusion molding the molten resin constantly forms the base while the ascending and descending movement of an ascending/descending member interrupts flow to the rib section resulting in a vertical line of a plurality of separate hook members 40 continuously extending from the backing substrate 42.

The invention microhooks generally have been formed to be particularly useful in engaging with low profile nonwoven laminates. Most notably improved engagement has been unexpectedly discovered where the hooks have relatively low arm droop, and the ratio of the arm droop to the thickness of the nonwoven portion of a nonwoven laminate is less than 1.5, preferably less than 1.3 and most dramatically when less than 1.0. The peel force (135 degree) is generally above 120 grams/2.5 cm, preferably greater than 200 grams/2.5 cm.

Suitable low profile nonwoven laminates are laminates of a nonwoven fabric or web to a film or a higher strength nonwoven fabric or web. A "nonwoven fabric or web" is a web of individual fibers or threads which are randomly associated fibers that are not associated in a regular manner such as in a knitted fabric. Nonwoven fabrics or webs can be formed from processes such as, for example, meltblowing, spunbonding, spunlace and bonded carded webs.

In a preferred embodiment, the laminate is a film/nonwoven laminate where the nonwoven fabric, preferably a spunbond web, is thermally or extrusion bonded to a film. The film can have a center bonding layer which is made from a polymer which more easily bonds to the nonwoven, such as a semi-crystalline/amorphous with a base layer of another polymer, such as a polyolefin. Pigments can also be used in the base layer.

Suitable bonding layers include polymers such as disclosed in European Patent Application EP 0444671 A3, European Patent application EP 0472946 A2, European Patent Application EP 0400333 A2, U.S. Pat. No. 5,302,454 and U.S. Pat. No. 5,368,927 and other bonding polymers include ethylene-n-butyl acetate, ethylene/vinyl acetate copolymers, ethylene/methyl acetate copolymers, ethyl acrylic acid and other copolymers, and terpolymers of polypropylene, polyethylene and polybutylene as well as elastomers such as styrene conjugated diene block copolymer such as SEBS, SEPS, SBS, and urethanes.

A base layer used with bonding layer may be a polypropylene polymer or copolymer. Since this layer is relatively thick, the majority of opacity if desired may be added to this layer through the use of opacifiers such as, for example, $TiO_2$ or $CaCO_3$. The nonwoven and the film or higher strength nonwoven component are preferably bonded together using thermal point bonding (heat or ultrasonic bonding). The point bonding if used should be at a density that would allow hooks to penetrate into the nonwoven, generally 30 percent or less, and preferably 20 percent or less. The lower bond area limit depends on the integrity of the laminate and the bond strength at the points but it is generally greater than 1 to 2 percent. A compatible tackifying resin may also be added to the bonding layer.

The nonwoven used in the laminates preferably is produced by meltblowing or spunbonding processes, which processes are well known in the art. The extruded fibers were generally deposited on a moving foraminous mat or belt to form the nonwoven fabric. The fibers produced in the spunbond and meltblown processes have average fiber diameters of less than 75 microns and less. Meltblown fibers are able to be produced having average fiber diameter of 10 microns and less, to about 1 micron. Spunbond fibers are generally 25 microns or more and are preferred for use to engage with the invention microhooks due to their greater strength. The nonwoven portion of the laminate generally has a thickness of from 100 to 300 microns, preferably from 100 to 200 microns and has a basis weight of from 10 to 50 g/m$^2$.

Test Methods

135 Degree Peel Test

The 135 degree peel test was used to measure the amount of force that was required to peel a sample of the mechanical fastener hook material from a sample of loop fastener material. A 5.1 cm×12.7 cm piece of a loop test material was securely placed on a 5.1 cm×12.7 cm steel panel by using a double-coated adhesive tape. The loop material was placed onto the panel with the cross direction of the loop material parallel to the long dimension of the panel. A 1.9 cm×2.5 cm strip of the mechanical fastener to be tested was cut with the long dimension being in the machine direction of the web. A 2.5 cm wide paper leader was attached to the smooth side of one end of the hook strip. The hook strip was then centrally placed on the loop so that there was a 1.9 cm×2.5 cm contact area between the strip and the loop material and the leading edge of the strip was along the length of the panel. The strip and loop material laminate was then rolled by hand, twice in each direction, using a 1000 gram roller at a rate of approximately 30.5 cm per minute. The sample was then placed in a 135 degree peel jig. The jig was placed into the bottom jaw of an Instron™ Model 1122 tensile tester. The loose end of the paper leader was placed in the upper jaw of the tensile tester. A crosshead speed of 30.5 cm per minute and a chart recorder set at a chart speed of 50.8 cm per minute was used to record the peel force as the hook strip was peeled from the loop material at a constant angle of 135 degrees. An average of the four highest peaks was recorded in grams. The force required to remove the mechanical fastener strip from the loop material was reported in grams/2.54 cm-width. A minimum of 10 tests were run and averaged for each hook and loop combination.

Two different loop materials were used to measure the performance of the mechanical fastener hook material. Loop material 'A' is a nonwoven loop made similar to that described in U.S. Pat. No. 5,616,394 Example 1, available from the 3M Company as KN-1971. Loop material 'B' is a knitted loop made similar to that described in U.S. Pat. No. 5,605,729, Example 1 available from the 3M Company as XML-01-160. The loop test materials were obtained from a supply roll of the material after unwinding and discarding several revolutions to expose "fresh" material. The loop test material thus obtained was in a relatively compressed state and was used immediately in the peel test before any significant relofting of the loops could occur.

135 Degree Peel Test for Low Profile Loops

A 135 degree peel test was used to measure the amount of force that was required to peel a sample of the mechanical fastener hook material from a sample of low profile loop fastener material. A 1.9 cm×2.5 cm strip of the mechanical fastener to be tested was cut with the long dimension being in the machine direction of the web. A 2.5 cm wide paper leader was attached to the smooth side of one end of the hook strip. The hook materials were fastened to the low profile loop material using the following procedure: The hook material, with hook side down, was placed onto the low profile loop backsheet material of a diaper. A 4.1 kg weight measuring 7.6 cm×7.6 cm with medium grit abrasive paper on the bottom surface, was placed on top of the hook material. To engage the hook with the backsheet loop material, the diaper was held securely flat and the weight was twisted 45 degrees to the right, then 90 degrees to the left, then 90 degrees right and then 45 degrees left. The weight was then removed and the diaper was held firm against the surface of a 135 degree jig stand mounted into the lower jaw of an Instron™ Model 1122 tensile tester. The loose end of the paper leader attached to the hook material was placed in the upper jaw of the tensile tester. A crosshead speed of 30.5 cm per minute and a chart recorder set at a chart speed of 50.8 cm per minute was used to record the peel force as the hook strip was peeled from the loop material at a constant angle of 135 degrees. An average of the four highest force peaks was recorded in grams and was reported in grams/2.54 cm-width. 10 different locations were tested on each diaper with the average of the 10 being reported in Table 4.

Three different low profile loop materials were used to measure the performance of the mechanical fastener hook material. Loop material 'C' is the nonwoven side (i.e. outward facing side) of the backsheet of a Loving Touch diaper size 3. Loop material 'D' is the nonwoven side (i.e. outward facing side) of the backsheet of a Walgreens Supreme diaper size 4. Loop material 'E', was cut from a Leggs Sheer Energy B nylon stocking. The fabric was stretched by hand approximately 200% and then attached to a 5 cm×15 cm steel panel using double-coated adhesive tape. The thickness of the fabric was measured in the stretched condition using an optical microscope. Twelve measurements were averaged to obtain a thickness of 239 microns.

Hook Dimensions

The dimensions of the Example and Comparative Example hook materials were measured using a Leica microscope equipped with a zoom lens at a magnification of approximately 25×. The samples were placed on a x-y moveable stage and measured via stage movement to the nearest micron. A minimum of 3 replicates were used and averaged for each dimension. In reference to the Example and Comparative Example hooks, as depicted generally in FIGS. 5, 6, 7, 11, 12, 13 and 14 hook width is indicated by distance 23, hook height is indicated by distance 20, arm droop is indicated by distance 24, and hook thickness is indicated by distance 21.

Molecular Orientation and Crystallinity

The orientation and crystallinity of the Example and comparative example hook materials were measured using X-ray diffraction techniques. Data was collected using a Bruker microdiffractometer (Bruker AXS, Madison, Wis.), using copper K$_\alpha$ radiation, and HiSTAR™ 2-dimensional detector registry of scattered radiation. The diffractometer was fitted with a graphite incident beam monochromator and a 200 micrometer pinhole collimator. The X-ray source consisted of a Rigaku RU200 (Rigaku USA, Danvers, Mass.) rotating anode and copper target operated at 50 kilovolts (kV) and 100 milliamperes (mA). Data was collected in transmission geometry with the detector centered at 0 degrees (2θ) and a sample to detector distance of 6 cm. Test specimens were obtained by cutting thin sections of the hook materials in the machine direction after removing the hook arms. The incident beam was normal to the plane of the cut sections and thus was parallel to the cross direction of the extruded web. Three different positions were measured using a laser pointer and digital video camera alignment system. Measurements were taken near the center of the head portion 17, near the midpoint of the stem portion 15, and as close as possible to the bottom of the stem portion 17 just slightly above the surface 12 of the backing 11. The data was accumulated for 3600 seconds and corrected for detector sensitivity and spatial linearity using GADDS™ software (Bruker AXS Madison, Wis.). The crystallinity indices were calculated as the ratio of crystalline peak area to total peak area (crystalline+amorphous) within a 6 to 32 degree (2θ) scattering angle range. A value of one represents 100 percent crystallinity and value of zero corresponds to completely amorphous material (0 percent crystallinity). The percent molecular orientation was calculated from the radial traces of the two-dimensional diffraction data. Background and amorphous intensities were assumed to be linear between the 2θ positions defined by traces (A) and (C) defined below. The background and amorphous intensities in trace (B) were interpolated for each element and subtracted from the trace to produce (B'). Plot of trace (B') has constant intensity in absence of orientation or oscillatory intensity pattern when preferred orientation present. The magnitude of the crystalline fraction possessing no preferred orientation is defined by the minimum in the oscillatory pattern. The magnitude of the oriented crystalline fraction is defined by the intensity exceeding the oscillatory pattern minimum. The percent orientation was calculated by integration of the individual components from trace (B').

Trace (A): leading background edge and amorphous intensity, 12.4–12.8 degrees (2θ) radially along χ, 0.5 degree step size.

Trace (B): random and oriented crystalline fractions, background scattering, and amorphous intensity; 13.8–14.8 degrees (2θ) radially along χ, 0.5 degree step size.

Trace (C): trailing background edge and amorphous intensity; 15.4 to 15.8 degrees (2θ) radially along χ, 0.5 degree step size.

Trace (B'): random and oriented crystalline fractions obtained by subtraction of amorphous and background intensity from trace (B).

scattering angle center of trace (A): (12.4 to 12.8) deg.=12.6 deg. 2θ center of trace (B): (13.8 to 14.8) deg.=14.3 deg. 2θ center of trace (C): (15.4 to 15.8) deg.=15.6 deg. 2θ

Interpolation constant=(14.3−12.6)/(15.6−12.6)=0.57 for each array element [i]:

$$\text{Intensity}_{(amorphous+background)}[i]=[(C[i]-A[i])*0.57]+A[i]$$

$$B'[i]=B[i]-\text{Intensity}_{(amorphous+background)}[i]$$

From a plot of B' [i] versus [i]:

$$B'_{(random)}[i]=\text{intensity value of minimum in oscillatory pattern}$$

$$B'_{(oriented)}[i]=B'[i]-B'_{(random)}[i]$$

Using a Simpson's Integration technique and the following areas the percent of oriented material was calculated.

$$B'[i]=\text{total crystalline area(random+oriented)}=\text{Area}_{(total)}$$

$$B'_{(oriented)}[i]=\text{oriented crystalline area}=\text{Area}_{(oriented)}$$

$$B'_{(random)}[i]=\text{random crystalline area}=\text{Area}_{(random)}$$

$$\%\text{ oriented material}=(\text{Area}_{(oriented)}/\text{Area}_{(total)})\times 100$$

COMPARATIVE EXAMPLE C1

A mechanical fastener hook material web was made using the apparatus shown in FIG. 1. A polypropylene/polyethylene impact copolymer (SRC7-644, 1.5 MFI, Dow Chemical) was extruded with a 6.35 cm single screw extruder (24:1 L/D) using a barrel temperature profile of 177° C.–232° C.–246° C. and a die temperature of approximately 235° C. The extrudate was extruded vertically downward through a die having an opening cut by electron discharge machining. After being shaped by the die, the extrudate is quenched in a water tank at a speed of 6.1 meter/min with the water being maintained at approximately 10° C. The web was then advanced through a cutting station where the ribs (but not the base layer) were transversely cut at an angle of 23 degrees measured from the transverse direction of the web. The spacing of the cuts was 305 microns. After cutting the ribs, the base of the web was longitudinally stretched at a stretch ratio of approximately 4.1 to 1 between a first pair of nip rolls and a second pair of nip rolls to further separate the individual hook elements to approximately 8 hooks/cm. There were approximately 10 rows of ribs or cut hooks per centimeter. The upper roll of the first pair of nip rolls was heated to 143° C. to soften the web prior to stretching. The general profile of this hook is depicted in FIG. 5.

EXAMPLE 1

The web of comparative example C1 was subjected to a non-contact heat treatment on the hook side of the web by passing said web underneath a 36 cm wide ribbon flame burner Aerogen (Alton Hampshire, UK) at a speed of 90 meter/minute with a burner to film gap of 8 mm. The flame power was 74 kJ/hour. The smooth base film side of the web was supported on a chill roll maintained at approximately 18° C. The general profiles of the resulting heat treated hook are depicted in FIGS. 6a and 6b. The performance of the hook material web against nonwoven loop material 'A' was measured using a 135° peel test with the results shown in Table 1 below. The peel force of the heat-treated web was approximately 63% greater than the non-heated Comparative Example 1.

EXAMPLE 2

Figure 7A:
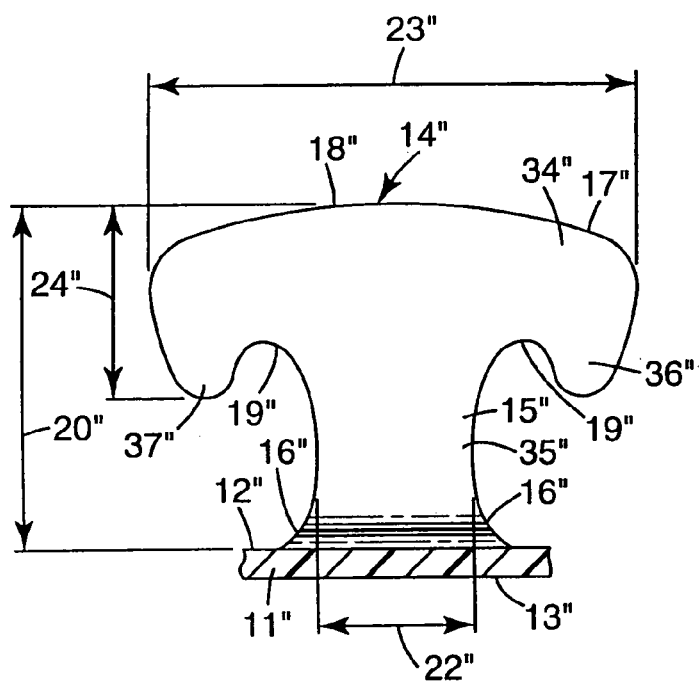
FIGS. 7a and 7b are views of FIGS. 5a and 5b, respectively, after heat treating of the entire hook member.
Figure 7B:
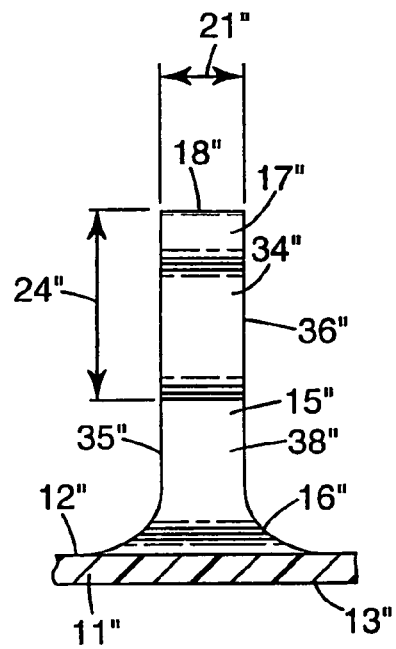

The web of Comparative Example C1 was subjected to a non-contact heat treatment on the hook side of the web by passing said web underneath a bank of 6–1000 watt 1 micron wavelength infrared bulbs at a speed of 2.1 meter/min. The hook to bulb spacing was approximately 2.5 cm. The smooth base film side of the web was supported on a chill roll maintained at approximately 66° C. The general profiles of the resulting heat treated hook are depicted in FIGS. 7a and 7b. The performance of the hook material web against nonwoven loop material 'A' was measured using a peel test with the results shown in Table 1 below. The 135° peel force of the heat-treated web was approximately 206% greater than the non-heat treated Comparative Example C1.

COMPARATIVE EXAMPLE C2

A mechanical fastener hook material web was made as in Comparative Example 1 except the web was extruded at a speed of 9.1 meter/min to increase the amount of melt flow induced molecular orientation in the extrudate. The general profile of this hook is depicted in FIG. 5.

EXAMPLE 3

The web of Comparative Example C2 was subjected to a non-contact heat treatment on the hook side of the web by passing said web underneath a bank of 6–2000 watt 1 micron wavelength infrared bulbs at a speed of 3.0 meter/min. The hook to bulb spacing was approximately 1.6 cm. The smooth base film side of the web was supported on a chill roll maintained at approximately 66° C. The performance of the hook material web against nonwoven loop material 'A' was measured using a peel test with the results shown in Table 1 below. The 135° peel force of the heat-treated web was approximately 37% greater than the non-heat treated Comparative Example C2.

COMPARATIVE EXAMPLE C3

Figure 11:
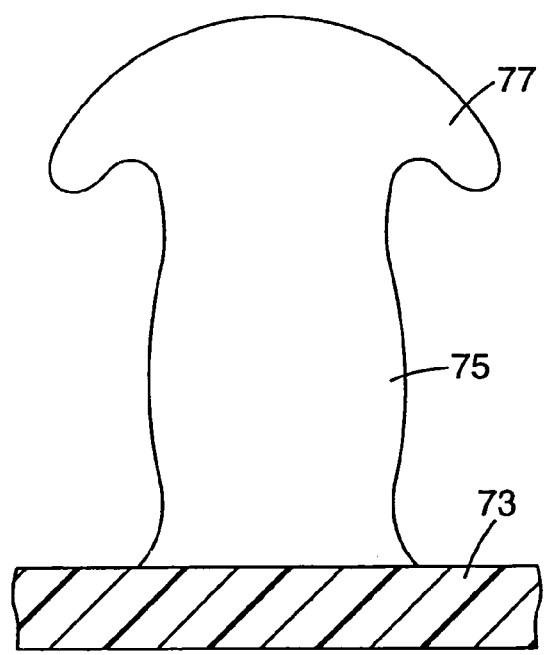
FIG. 11 is a cross-sectional view of a fully heat treated alternative hook member in accordance with the invention.
Figure 12:
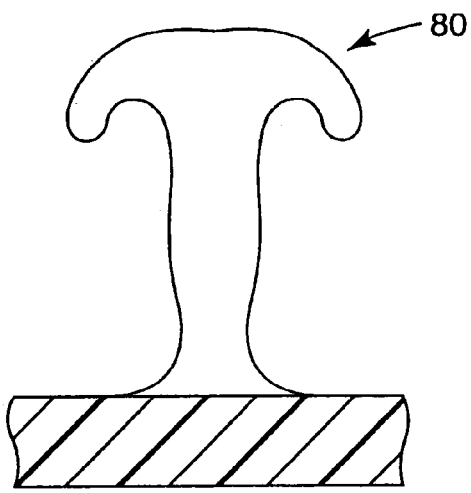
FIG. 12 is a cross-sectional view of a heat treated hook member in accordance with the invention.

A mechanical fastener hook material web was made as in Comparative Example 1 except the extrudate was pulled from the die lip at a 20 degree angle from vertical so as to produce a cross-sectional profile as shown in FIG. 11. Hook spacing was 16 rows of hooks per centimeter.

EXAMPLE 4

The web of Comparative Example C3 was subjected to a non-contact heat treatment on the hook side of the web by passing said web underneath a bank of 3–4500 watt 3 micron wavelength infrared bulbs at a speed of 10.0 meter/min producing hook members such as shown in FIG. 11 with a hook head portion 77 and stem portion 75 and a base 73. The hook to bulb spacing was approximately 2.5 cm. The smooth base film side of the web was supported on a chill roll maintained at approximately 66° C. The performance of the hook material web against nonwoven loop material 'A' was measured using a 135° peel test with the results shown in Table 1 below. The peel force of the heat-treated web was approximately 254% greater than the non-heat treated Comparative Example C3.

EXAMPLE 5

The web of Comparative Example C3 was subjected to a non-contact heat treatment on the hook side of the web by passing said web underneath a perforated metal plate at a speed of 25.0 meter/min producing hook members having a profile substantially as shown in FIG. 11. Hot air at a temperature of approximately 185° C., provided by a 15 kW electric heater, was blown through the perforations in the metal plate onto the hook side of the web at a velocity of approximately 3350 meter/min. The hooks were approximately 46 cm from the perforated plate. The smooth base film side of the web was supported on a chill roll at approximately 149° C. After heat treatment the web was cooled by passing the web over a chill roll maintained at 11° C. The performance of the hook material web against nonwoven loop material 'A' was measured using a 135° peel test with the results shown in Table 1 below. The peel force of the heat-treated web was approximately 136% greater than the non-heat treated Comparative Example C3.

COMPARATIVE EXAMPLE C4

Figure 14:
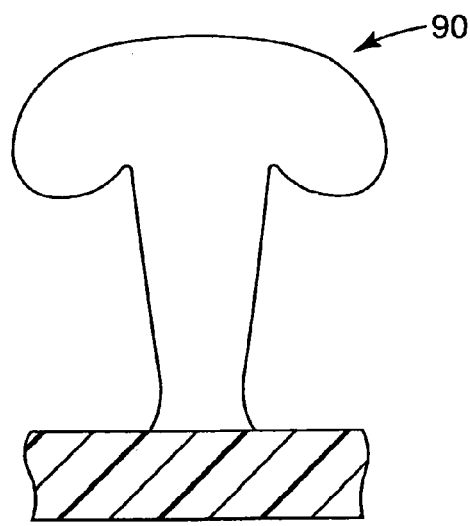
FIG. 14 is a cross-sectional view of a fully heat treated hook member in accordance with the invention.

A mechanical fastener hook material web was made as in comparative example 1 except the opening in the die was shaped as shown in FIG. 14 (after heat treating) and the spacing of the cuts was 267 microns prior to stretching the web.

EXAMPLE 6

The web of comparative example C4 was subjected to a non-contact heat treatment on the hook side of the web by passing said web underneath a bank of 3–4500 watt 3 micron wavelength infrared bulbs at a speed of 10.0 meter/min producing hook members 90 such as shown in FIG. 14. The hook to bulb spacing was approximately 2.5 cm. The smooth base film side of the web was supported on a chill roll maintained at approximately 66° C. The performance of the hook material web against nonwoven loop material 'A' and knitted loop material 'B' was measured using a 135° peel test with the results shown in Table 1 below. The peel force of the heat-treated web using loop material 'A' was approximately 112% greater than the non-heat treated Comparative Example C4 and 32% greater when using loop material 'B'.

COMPARATIVE EXAMPLE C5

A mechanical fastener hook material web was made as in Comparative Example 1 except a high density polyethylene resin (D450 4.5 MI, 0.942 density, Chevron Philips) blended with 2% M1350 silicone/PP masterbatch (Dow Corning) processing aid was used to form the extrudate at a melt temperature of approximately 238° C. The opening in the die was shaped to produce the profile 80 depicted in FIG. 12. After quenching the extrudate and cutting of the ribs the web was oriented in the machine direction 3.5:1.

COMPARATIVE EXAMPLE C6

A mechanical fastener hook material web, available from the 3M Corporation as KN-3425, was made similar to Comparative Example 1. The dimensions of the hook material are shown in Table 3.

EXAMPLE 7

Figure 13:
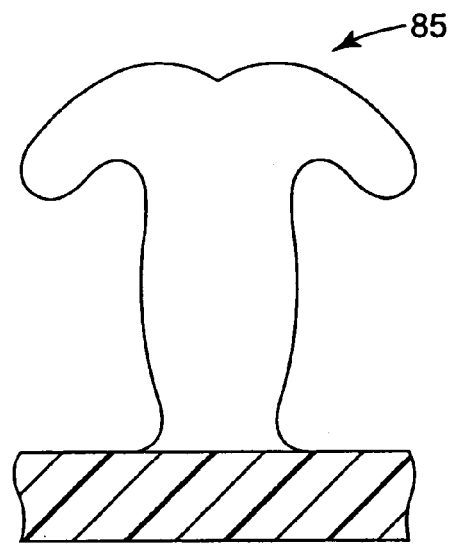
FIG. 13 is a cross-sectional view of a fully heat treated hook member in accordance with the invention.

The web of Comparative Example C5 was subjected to a non-contact heat treatment on the hook side of the web by passing said web underneath a bank of 6–2000 watt 1 micron wavelength infrared bulbs at a speed of 4.0 meter/min producing hook member 85, substantially as shown in FIG. 13. The hook to bulb spacing was approximately 1.6 cm. The smooth base film side of the web was supported on a chill roll maintained at approximately 66° C. The performance of the hook material web against nonwoven loop material 'A' was measured using a 135° peel test with the results shown in Table 1 below. The peel force of the heat-treated web was approximately 151% greater than the non-heat treated Comparative Example C5.

EXAMPLE 8

A web was made similar to Comparative Example C3 except the extrudate was pulled from the die lip at a 20 degree angle from vertical so as to produce a slightly different cross-sectional profile. The web was subjected to a non-contact heat treatment on the hook side of the web by passing said web underneath a perforated metal plate at a speed of 25.0 meter/min producing hook members having a profile substantially as shown in FIG. 11. Hot air at a temperature of approximately 185° C., provided by a 15 kW electric heater, was blown through the perforations in the metal plate onto the hook side of the web at a velocity of approximately 3350 meter/min. The hooks were approximately 46 cm from the perforated plate. The smooth base film side of the web was supported on a chill roll at approximately 149° C. After heat treatment the web was cooled by passing the web over a chill roll maintained at 11° C. The dimensions of the resulting heat-treated hook material are shown in Table 3 below and the peel performance against low profile loops is shown in Table 4. The peel force of the heat-treated web was approximately 62% and 60% greater respectively, for low profile loops 'C' and 'D', than the non-heat treated Comparative Example C6.

EXAMPLE 9

A web was made similar to Comparative Example C3 except the extrudate was pulled vertically from the die lip. The web was subjected to a non-contact heat treatment on the hook side of the web by passing said web underneath a perforated metal plate at a speed of 25.0 meter/min producing hook members having a profile substantially as shown in FIG. 11. Hot air at a temperature of approximately 185° C., provided by a 15 kW electric heater, was blown through the perforations in the metal plate onto the hook side of the web at a velocity of approximately 3350 meter/min. The hooks were approximately 46 cm from the perforated plate. The smooth base film side of the web was supported on a chill roll at approximately 149° C. After heat treatment, the web was cooled by passing the web over a chill roll maintained at 11° C. The dimensions of the resulting heat-treated hook material are shown in Table 3 below and the peel performance against low profile loops is shown in Table 4. The peel force of the heat-treated web was approximately 140% and 107% greater respectively, for low profile loops 'C' and 'D', than the non-heat treated Comparative Example C6.

EXAMPLE 10

A web was made similar to Comparative Example C3 except a different die plate was used to produce a tapered stem having a larger width at the base of the stem than at the top of the stem. The web was subjected to a non-contact heat treatment on the hook side of the web using the following procedure. A 13 cm×43 cm piece of web was placed onto a 13 cm×43 cm steel plate (1.3 cm thick), hook-side up, and edge clamped to prevent the web from shrinking. Hot air from a Master brand hot air gun at 400° C. was blown vertically down onto the web by passing the air gun uniformly over the web for about 10 seconds. The dimensions of the resulting heat-treated hook material are shown in Table 3 below and the peel performance against low profile loops is shown in Table 4. The peel force of the heat-treated web was approximately 321% and 177% greater respectively, for low profile loops 'C' and 'D', than the non-heat treated Comparative Example C6.

EXAMPLE 11

A web was made similar to the web of Comparative Example C1 except the base of the web was longitudinally stretched at a stretch ratio of approximately 3.65 to 1 between a first pair of nip rolls and a second pair of nip rolls to further separate the individual hook elements to approximately 8.5 hooks/cm. There were approximately 15 rows of ribs or cut hooks per centimeter. The web was then subjected to a non-contact heat treatment on the hook side of the web by passing said web underneath a perforated metal plate at a speed of 8.9 meter/min producing hook members having a profile similar to those in Example 9 and shown in FIG. 11. Hot air at a temperature of approximately 185° C., provided by a 15 kW electric heater, was blown through the perforations in the metal plate onto the hook side of the web at a velocity of approximately 3350 meter/min. The hooks were approximately 46 cm from the perforated plate. The smooth base film side of the web was supported on a chill roll at approximately 149° C. After heat treatment the web was cooled by passing the web over a chill roll maintained at 1° C.

EXAMPLE 12

A web was made similar to the web of Example 11 except the web was longitudinally stretched at a stretch ratio of approximately 2.5 to 1 between a first pair of nip rolls and a second pair of nip rolls prior to the cutting step to increase orientation of the web prior to cutting of the ribs. The upper roll of the first pair of nip rolls was heated to 143° C. to soften the web prior to stretching. After stretching, the web was cut as in Example 11 and then longitudinally stretched at a stretch ratio of approximately 3.65 to 1 between a first pair of nip rolls and a second pair of nip rolls to further separate the individual hook elements to approximately 8.5 hooks/cm. The web was then subjected to a non-contact heat treatment on the hook side of the web as described in Example 11.

TABLE 1

| Hook Material | Hook width (μm) | Hook Height (μm) | Arm Droop (μm) | Hook Thickness (μm) | Peel Force Loop 'A' (grams) | Peel Force Loop 'B' (grams) |
|---|---|---|---|---|---|---|
| C1 | 536 | 573 | 217 | 340 | 202 | — |
| 1 | 663 | 582 | 301 | 85 | 329 | — |
| 2 | 682 | 606 | 341 | 179 | 619 | — |
| C2 | 479 | 512 | 147 | 309 | 164 | — |
| 3 | 703 | 678 | 229 | 133 | 225 | — |
| C3 | 395 | 514 | 128 | 274 | 270 | — |
| 4 | 483 | 641 | 193 | 171 | 955 | — |
| 5 | 481 | 665 | 172 | 180 | 638 | — |
| C4 | 611 | 819 | 262 | 257 | 382 | 541 |
| 6 | 774 | 992 | 399 | 154 | 811 | 716 |
| C5 | 448 | 500 | 143 | 341 | 186 | — |
| 7 | 547 | 526 | 174 | 201 | 466 | — |

Comparative Example C2 and Example 3 were measured to show the change in molecular orientation and crystallinity due to heat treatment of the webs of the invention. The results are shown in Table 2 below. When heat is applied to the oriented hook elements, the molecular orientation decreases dramatically from the top down to the base, and crystallinity increases due to annealing effects.

TABLE 2

| Hook Material | Crystalline Index (top) | % Molecular Orientation (top) | % Molecular Orientation (body) | % Molecular Orientation (base) |
|---|---|---|---|---|
| C2 | 0.30 | 36.3 | 52.0 | 85.6 |
| 3 | 0.39 | 0.0 | 0.0 | 80.4 |

EXAMPLE 13

To obtain a fastener web having low hook density, a web was made similar to the web of Example 9 except C104 polypropylene/polyethylene impact copolymer (1.2 MFI, Dow Chemical, Midland, Mich.) was used as the extrudate. A white color concentrate (50:50 TiO2/PP) was added to the extruder at a 1% loading. The web was quenched and cut as in Example 9. The general profile of the individual hook elements is shown in FIG. 11. The web was then subjected to a biaxial stretching (2×2) using a KARO 4 pantograph stretcher (Bruckner GmbH). A 115 mm×115 mm sample of the web was preheated at a temperature of 130° C. for 60 seconds followed by 2×2 stretching at a stretch rate of 100%/second. The hook spacing in the machine direction was approximately 21.3 hooks/cm and 7 hooks/cm in the cross direction. The web was then subjected to a non-contact heat treatment on the hook side of the web using the following procedure. A 13 cm×43 cm piece of web was placed onto a 13 cm×23 cm steel plate (1.3 cm thick), hook-side up, and edge clamped to prevent the web from shrinking. Hot air from a 14.5 amperage Master brand hot air gun at 400° C. with a vent setting of 50%, was blown vertically down onto the web by passing the air gun uniformly over the web for about 20 seconds. The dimensions of the resulting heat-treated hook material are shown in Table 3 below.

EXAMPLE 14

To obtain a fastener web having even lower hook density, a web was made similar to the web of Example 13 except the web was subjected to a 3×3 biaxial stretching using a KARO 4 pantograph stretcher. The hook spacing in the machine direction was approximately 12.3 hooks/cm and 4.3 hook/cm in the cross direction. The dimensions of the resulting heat-treated hook material are shown in Table 3 below.

Table 3 below shows the effect of non-contact heat treatment on hook dimensions. Hook thickness decreases dramatically upon the application of heat to hooks having significant molecular orientation.

TABLE 3

| Hook Material | Hook width (μm) | Hook Height (μm) | Arm Droop (μm) | Hook Thickness (μm) | Hooks/ cm CD | Stem Width (base) (μm) | Stem Width (top) (μm) |
|---|---|---|---|---|---|---|---|
| C6 | 521 | 485 | 246 | 343 | 10 | 232 | 231 |
| 8 | 487 | 511 | 176 | 101 | 14 | 233 | 242 |
| 9 | 544 | 426 | 136 | 98 | 14.2 | 227 | 279 |
| 10 | 384 | 645 | 112 | 122 | 18.9 | 247 | 153 |
| 11 | 470 | 555 | 113 | 143 | 14.7 | 240 | 228 |
| 12 | 449 | 487 | 117 | 70 | 23.8 | 196 | 217 |
| 13 | 571 | 617 | 135 | 94 | 7.0 | — | — |
| 14 | 607 | 617 | 132 | 113 | 4.3 | — | — |

The thicknesses of the low profile loops 'C' and 'D' were determined from scanning electron microscopic (SEM) photos. The nonwoven diaper backsheets were carefully cut with a razor and SEM photos were taken of the cross-section. The distance from the loop/film interface to the top of the loop pile was measured with a ruler from the photographs and converted to microns. Three locations were measured for three different replicates. The nine readings were averaged and are reported below.

Table 4 below shows that as the ratio of hook arm droop to loop thickness decreases, the peel force to thin, low profile nonwoven loops increases dramatically.

TABLE 4

| | Loop Thickness (μm) | | | Arm Droop/Loop Thickness Ratio | | | Peel Force (gms/2.5 cm) | | |
|---|---|---|---|---|---|---|---|---|---|
| Hook Material | Loop C | Loop D | Loop E | Loop C | Loop D | Loop E | Loop C | Loop D | Loop E |
| C6 | 133 | 154 | 239 | 1.85 | 1.6 | 1.03 | 78 | 110 | 308 |
| 8 | 133 | 154 | 239 | 1.32 | 1.14 | 0.74 | 126 | 176 | 409 |
| 9 | 133 | 154 | 239 | 1.02 | 0.88 | 0.57 | 187 | 228 | 533 |
| 10 | 133 | 154 | 239 | 0.84 | 0.73 | 0.47 | 328 | 305 | 542 |

Table 5 below shows the peel force of low hook density examples 13 and 14 peeled from low profile nonwoven loop 'C' using the 135 Degree Peel Test for Low Profile Loops described above. The actual number of individual hooks per tab was calculated and then divided into the peel force to obtain the peel force per individual hook member.

TABLE 5

| Hook Material | Peel Force Loop 'C' (grams/2.54 cm) | # Hooks/ test tab | Peel Force/individual hook (grams/hook) |
|---|---|---|---|
| 13 | 152 | 722 | 0.21 |
| 14 | 116 | 256 | 0.51 |

CONTROL EXAMPLE 15

A mechanical fastener hook material web was made using the apparatus shown in FIG. 1. A polyethylene resin (DFDB 6005, 0.2 MFI, 0.92 density, Dow Chemical Corp., Midland, Mich.) pigmented with 1% $TiO_2$ color concentrate (15100P, Clariant Corp., Minneapolis, Minn.) was extruded with a 6.35 cm single screw extruder (24:1 L/D) using a barrel temperature profile of 177° C.–232° C.–246° C. and a die temperature of approximately 235° C. The extrudate was extruded vertically downward through a die having an opening cut by electron discharge machining. After being shaped by the die, the extrudate was quenched in a water tank at a speed of 6.1 meter/min with the water being maintained at approximately 10° C. The web was then advanced through a cutting station where the ribs (but not the base layer) were transversely cut at an angle of 23 degrees measured from the transverse direction of the web. The spacing of the cuts was 305 microns. After cutting the ribs, the base of the web was longitudinally stretched at a stretch ratio of approximately 3 to 1 between a first pair of nip rolls and a second pair of nip rolls to further separate the individual hook elements to approximately 10 hooks/cm. There were approximately 15 rows of ribs or cut hooks per centimeter. The upper roll of the first pair of nip rolls was heated to 100° C. to soften the web prior to stretching. The general profile of this hook is depicted in FIG. 11. The web was then subjected to a non-contact heat treatment on the hook side of the web using the following procedure. A 13 cm×43 cm piece of web was placed onto a 13 cm×43 cm steel plate (1.3 cm thick), hook-side up, and edge clamped to prevent the web from shrinking. Hot air from a Master brand hot air gun at 400° C. was blown vertically down onto the web by passing the air gun uniformly over the web for about 10 seconds. The width (thickness) of the hooks was measured before and after heat treating and is shown in Table 6 below.

EXAMPLE 16

A hook web was made similar to that of Control Example 15 except 50% polypropylene/polyethylene impact copolymer (C104 1.2 MFI, Dow Chemical Corp., Midland, Mich.) was blended with the DFDB 6005 polyethylene resulting in a composition of PE:PP:PE:TiO2 concentrate (15100P) in a ratio of 49.5:49.5:1.0. The web was heat treated in the same manner as Control Example 15. The decrease in hook thickness after heat treatment of the blended hook material was 9.1% greater than the non-blended hook material.

CONTROL EXAMPLE 17

A hook web was made similar to that of Control Example 15 except 99% polypropylene/polyethylene impact copolymer (C104) pigmented with 1% $TiO_2$ color concentrate (15100P) was used as the extrudate. The die plate used was described in Example 10. The spacing of the cuts was 250 microns. The web was heat treated in the same manner as Control Example 15. The performance of the hook material web against nonwoven loop material 'A' was measured using a peel test with the results shown in Table 6 below.

EXAMPLE 18

A hook web was made similar to that of Control Example 17 except 10% SIS block copolymer (KRATON 1119, Kraton Polymers, Houston, Tex., USA) was blended with the C104 polypropylene resulting in a composition of PP:SIS:$TiO_2$ concentrate (15100P) in a ratio of 89:10:1. The web was heat treated in the same manner as Control Example 17. The decrease in hook thickness after heat treatment of the blended hook material was 7.5% greater than the non-blended hook material. The 135° peel force of the heat-treated blended web was approximately 68% greater than the non-blended Control Example 17.

CONTROL EXAMPLE 19

A hook web was made similar to that of Control Example 15 except 99% polypropylene/polyethylene impact copolymer (SRC-7644, Dow Chemical Co., Midland, Mich.) pigmented with 1% $TiO_2$ color concentrate (15100P) was used as the extrudate and different cutting conditions were used to produce a thicker hook. The web was heat treated in the same manner as Control Example 15. The performance of the hook material web against nonwoven loop material 'A' was measured using a 135° peel test with the results shown in Table 6 below.

EXAMPLE 20

A hook web was made similar to that of Control Example 19 except 5% KRATON 1119, 5% FORAL NC tackifier (Hercules Chemical, Wilmington, Del.) and 1% 15100P $TiO_2$ was blended with 89% SRC-7644 polypropylene/polyethylene impact copolymer to form the extrudate. The web was heat treated in the same manner as Control Example 15. The decrease in hook thickness after heat treatment of the blended hook material was 13.4% greater than the non-blended hook material. The 135° peel force of the heat-treated blended web was approximately 63% greater than the non-blended Control Example 19.

EXAMPLE 21

A hook web was made similar to that of Example 20 except a precompounded resin blend consisting of 65% 5D45 polypropylene (0.7 g/min MFI, Dow Chemical Co., Midland, Mich.), 35% mineral oil (Superla White No. 31, Chevron Texaco, San Ramon, Calif., USA) and 0.1% Millad 3988 nucleating agent (Milliken Chemical Co., Inman S.C.) was to form the extrudate. The web was heat treated in the same manner as Control Example 15. The decrease in hook thickness after heat treatment of the blended hook material was 69.3%.

EXAMPLE 22

A hook web was made similar to that of Control Example 17 except a coextrusion process was used to produce a web wherein the hook rails were foamed and the base film layer was unfoamed. A blend of 49% C104 copolymer, 49% FH3400 polypropylene and 2% chemical blowing agent concentrate (FM1307H) was extruded with a 3.8 cm single screw extruder (28:1 L/D) using a "humped" barrel temperature profile of 135° C.–210° C.–177° C. to form the hook rails. 100% 7C06 impact copolymer (Union Carbide Corp., Danbury, Conn.) was used to form the non-foamed base film layer and was extruded with a 6.35 cm single screw extruder (24:1 L/D) using a sloped barrel profile of 204° C. in the feed zone to 232° C. in the last zone. The melt streams of the two extruders were fed to a three layer coextrusion feedblock (Cloeren Co., Orange, Tex.) with the third layer inlet blocked such that a two layer output resulted. The feedblock was mounted onto an extrusion die equipped with a profiled die lip. The feedblock and die were maintained at 204° C. After being shaped by the die lip, the extrudate was quenched in a water tank at a speed of 4.6 meter/min with the water being maintained at approximately 16° C.–20° C. The resulting structure had a non-foamed base film layer with upstanding hook rails that were foamed approximately 70% of their height as measured from the top downward towards the base. The resulting structure had a 10% overall void content. The mean cell size of the foam cells in the foamed portion was 50 microns. The web was then advanced through a cutting station where the ribs (but not the base layer) were transversely cut at an angle of 23 degrees measured from the transverse direction of the web. The spacing of the cuts was 250 microns. After cutting the ribs, the base of the web was longitudinally stretched at a stretch ratio of approximately 3 to 1 between a first pair of nip rolls and a second pair of nip rolls to further separate the individual hook elements to approximately 10 hooks/cm. The upper roll of the first pair of nip rolls was heated to 100° C. to soften the web prior to stretching. There were approximately 15 rows of ribs or cut hooks per centimeter. The base film layer had a thickness of approximately 75 microns. The web was heat treated in the same manner as Control Example 15. The decrease in hook thickness after heat treatment of the hook material was 75%. The performance of the hook material web against nonwoven loop material 'B' was measured using a 135° peel test for low profile loops with the results shown in Table 6 below. The 135° peel force of the heat-treated foamed web was approximately 82% greater than the non-heat treated foamed web.

TABLE 6

| Hook Material | Initial Hook Thickness (μm) | Heat Treated Hook Thickness (μm) | % Change in Hook Thickness (μm) | Peel Force Loop 'A' (grams/ 2.5 cm) | Peel Force Loop 'B' (grams/ 2.5 cm) |
|---|---|---|---|---|---|
| Control 15 | 281 | 144 | 48.7 | | |
| 16 | 292 | 123 | 57.8 | | |
| Control 17 | 254 | 146 | 42.4 | 419 | |
| 18 | 254 | 129 | 49.5 | 706 | |
| Control 19 | 330 | 143 | 56.6 | 550 | |
| 20 | 330 | 98 | 70.0 | 896 | |
| 21 | 336 | 103 | 69.3 | | |
| 22 | 305 | 76 | 75 | | 209 |

We claim:

1. A unitary hook fastener of a resiliently flexible, polymeric resin comprising a base film portion having generally parallel upper and lower major surfaces, with at least 50 spaced hook members per square centimeter projecting from the upper surface of said base, said hook members having a height from said upper surface of less than 1000 μm and each comprising a stem portion attached at one end to said base, and a head portion at the end of said stem portion opposite said base said hook head portion projecting on opposite sides of the stem portion, at least the head portions having a thickness of from 50 to 2.00 μm in a first direction generally parallel to the surfaces of said base, wherein at least the hook head portion has a molecular orientation of less than 10 percent.

2. The unitary hook fastener of claim 1 wherein said stem portion has a width in the range of 50 to 500 μm in a second direction generally at a right angle to said first direction and parallel to the surfaces of said backing; said hook head portion having a width greater than said stem portion and a total width of from 100 to 800 μm in said second direction and an arm droop of front 100 to 500 μm.

3. A unitary hook fastener according to claim 2 having in the range of 50 to 300 spaced hook members per square centimeter.

4. The unitary hook fastener according to claim 2 wherein the hook head portion thickness is substantially the same as the stem portion thickness below the hook portion.

5. The unitary hook fastener according to claim 2 wherein the hook head portion thickness is less than a stem portion thickness below the hook head portion.

6. The unitary hook fastener according to claim 5 wherein the hook head portion has an arm extending past the stem portion the hook head portion arm varies in thickness from a tip of the hook head portion arm to a portion of the hook head portion arm adjacent the stem.

7. A unitary hook fastener according to claim 1 having in the range of 70 to 150 spaced hook members per square centimeter.

8. A unitary hook fastener according to claim 1 wherein said polymeric material is a thermoplastic resin and the hook head portion has rounded corners.

9. A unitary hook fastener according to claim 8 wherein said base portion has a general uniform thickness between said upper and lower surfaces of between 30 to 200 μm.

10. A unitary hook fastener accordion to claim 9 wherein said polymeric material comprises polyethylene, polypropylene, polypropylenepolyethylene copolyrmers or blends thereof.

11. A unitary book fastener according to claim 1 wherein said polymeric resin is a phase distinct blend of a first continuous phase of thermoplastic resin and a second distinct phase.

12. A unitary hook fastener according to claim 11 wherein said second distinct phase is a nonparticulate filler.

13. A unitary hook fastener accordion to claim 12 wherein said filler is a nonparticulate filler comprising from 20 to 50 percent by volume of the polymeric resin.

14. A unitary hook fastener according to claim 11 wherein said second phase is a gas.

15. A unitary hook fastener according to claim 11 wherein said second phase is a distinct incompatible polymer phase.

16. The unitary hook fastener according to claim 1 wherein the stem portion adjacent the base portion has a molecular orientation of at least 10 percent.

17. The unitary hook fastener according to claim 1 wherein the base film portion has a degree of molecular orientation in at least one direction.

18. The unitary hook fastener according to claim 1 wherein the base film portion has a degree of molecular orientation in two directions.

19. A fastener of a resiliently flexible, polymeric resin comprising a base film portion having generally parallel upper and lower major surfaces, with spaced upstanding projections projecting from the upper surface of said base, wherein at least a portion of the projections at an upper portion have a molecular orientation of less than 10 percent and adjacent the base film portion have a molecular orientation of greater than 10 percent.

20. The fastener of claim 19 wherein a portion of the upstanding projections have a molecular orientation of greater than 10 percent.

21. The fastener of claim 19 wherein a portion of the upstanding projections have a molecular orientation of from 20 to 100 percent.

22. A fastener according to claim 19 wherein a hook head portion thickness is less than a stem portion thickness below the hook head portion.

23. A fastener according to claim 19 wherein the hook head portion thickness is substantially the same as the stem portion thickness below the hook bead portion.

24. A fastener according to claim 19 wherein the hook head portion has an arm extending past the stem portion the hook head portion arm varies in thickness from a tip of the book head portion arm to a portion of the hook head portion arm adjacent the stem portion.

25. A fastener according to claim 19 wherein said polymeric resin is a phase distinct blend of a first continuous phase of thermoplastic resin and a second distinct phase.

26. A fastener according to claim 25 wherein said second distinct phase is a nonparticulate filler.

27. A fastener according to claim 26 wherein said filler is a nonparticulate filler comprising from 20 to 50 percent by volume of the polymeric resin.

28. A fastener according to claim 25 wherein said second phase is a gas.

29. A fastener according to claim 25 wherein said second phase is a distinct incompatible polymer phase.

30. A hook and loop fastener system of a unitary hook fastener and a low profile loop laminate, the unitary hook fastener comprising a base having generally parallel upper and lower major surfaces, with at least 50 spaced hook members per square centimeter projecting from the upper surface of said base, said hook members having a height from said upper surface of less than 1000 μm and each comprising a stem portion attached at one end to said base, and a hook head portion at the end of said stem portion opposite said base said hook head portion projecting on opposite sides of the stem portion, the hook head portion having a thickness of from 60 to 180 μm and an arm droop of from 50 to 700 μm, the loop laminate comprising a fibrous loop web bonded to a backing layer wherein the loop web has a thickness of from 100 to 300 microns and wherein the ratio of the arm droop to the loop web thickness is 1.5 or less, wherein at least the hook head portion has a molecular orientation of less than 10 percent.

31. A hook and loop fastener system of claim 30 wherein the hook head portion has a thickness of from 50 to 200 μm in a first direction generally parallel to the surface of said backing and the loop web is a nonwoven loop web formed of a nonwoven fibrous web having a thickness of from 100 to 300 microns.

32. The hook and loop fastener system of claim 31 wherein the backing layer is a film layer and the loop web is a nonwoven web point bonded to the film layer.

33. The hook and loop fastener system of claim 32 wherein the backing layer is a coextruded film layer having a bonding layer attached to said nonwoven fibrous web.

34. The hook and loop fastener system of claim 33 wherein the nonwoven web is spunbond nonwoven web.

35. A hook and loop fastener system of claim 31 wherein the hook head portion thickness is substantially the same as the stem portion thickness below the hook portion.

36. A hook and loop fastener system of claim 31 wherein the hook head portion thickness is less than a stem portion thickness below the hook portion.

37. A hook and loop fastener system of claim 36 wherein the hook head portion has an arm extending past the stem portion the hook head portion arm varies in thickness from a tip of the hook portion arm to a portion of the hook head portion arm adjacent the stem.

38. The hook and loop fastener system of claim 31 wherein the ratio of arm droop to nonwoven web thickness is 1.3 or less.

39. The hook and loop fastener system of claim 31 wherein the ratio of arm droop to nonwoven web thickness is 1.0 or less.

40. The hook and loop fastener system of claim 31 wherein said stem portion has a width in the range of 50 to 500 μm in a second direction generally at a right angle to said first direction and parallel to the surfaces of said backing; said hook head portion having a width greater than said stem portion and a total width of front 100 to 800 μm in said second direction and an arm droop of from 100 to 500 μm.

41. The hook and loop fastener of claim 31 wherein the hook head portion thickness is front 60 to 80 μm.

42. A hock and loop fastener system of claim 31 wherein the hook head portion thickness is from 50 to 80 μm having in the range of 50 to 300 spaced hook members per square centimeter.

43. A hook and loop fastener system of claim 31 wherein said polymeric material is a thermoplastic resin and the hook head portion has rounded corners.

44. A hook and loop fastener system of claim 43 wherein said base has a generally uniform thickness between said upper and lower surfaces of between 30 to 200 μm.

45. A hook and loop fastener system of claim 44 wherein said polymeric material comprises polyethylene, polypropylene, polyethylenepolyethylene copolymers or blends thereof.

46. A hook and loop fastener system of claim 30 wherein the stem portion adjacent the base has a molecular orientation of at least 10 percent.

47. A hook and loop fastener system of claim 30 wherein the system has a 135 degree peel force of greater than 120 g2.5 cm.

48. A hook and loop fastener system of claim 30 wherein the system has a 135 degree peel force of greater than 200 g/2.5 cm.

49. A hook and loop fastener system of claim 30 wherein the hook and loop fastener system is on a garment.

50. A unitary hook fastener of a resiliently flexible, polymeric resin comprising a base film portion having generally parallel upper and lower major surfaces, with at least 50 spaced hook members per square centimeter projecting from the upper surface of said base, said hook members having a height from said upper surface of less than 1000 μm and each comprising a stem portion attached at one end to said base, and a head portion at the end of said stem portion opposite said base, at least the head portions having a thickness of from 50 to 200 μm in a first direction generally parallel to the surfaces of said base, wherein
said polymeric resin is a phase distinct blend of a first continuous phase of thermoplastic resin and a second distinct phase.

* * * * *

UNITED STATES PATENT AND TRADEMARK OFFICE
CERTIFICATE OF CORRECTION

PATENT NO. : 7,185,401 B2
APPLICATION NO. : 11/016993
DATED : March 6, 2007
INVENTOR(S) : Ronald W. Ausen It is certified that error appears in the above-identified patent and that said Letters Patent is hereby corrected as shown below:

Column 2,
Title Page; Page 2: item (56) Line 20, Delete "Muraski" and insert -- Murasaki --, therefor.
Title Page; Page 2: item (56) Line 22, Delete "Appleton" and insert -- Paul Datta --, therefor.

Column 15,
Line 36, After "intensity" delete "," and insert -- ; --, therefor.

Column 18,
Line 34, Delete "M1350" and insert -- MB50 --, therefor.

Column 20,
Line 24-25, Delete "1°C" and insert -- 11°C --, therefor.

Column 21,
Line 17, Delete "TiO2/PP)" and insert -- TiO$_2$/PP) --, therefor.

Column 25,
Line 29, In Claim 1, delete "2.00" and insert -- 200 --, therefor.
Line 38, In Claim 2, delete "stern" and insert -- stem --, therefor.
Line 40, In Claim 2, delete "front" and insert -- from --, therefor.
Line 62, In Claim 9, delete "general" and insert -- generally --, therefor.
Line 64, In Claim 10, delete "accordion" and insert -- according --, therefor.
Line 66, In Claim 10, delete "polypropylenepolyethylene" and insert
-- polypropylene-polyethylene --, therefor.
Line 66, In Claim 10, delete "copolyrmers" and insert -- copolymers --, therefor.

Column 26,
Line 1, In Claim 11, delete "book" and insert -- hook --, therefor.
Line 7, In Claim 13, delete "accordion" and insert -- according --, therefor.
Line 42, In Claim 23, delete "bead" and insert -- head --, therefor.
Line 46, In Claim 24, delete "book" and insert -- hook --, therefor.

UNITED STATES PATENT AND TRADEMARK OFFICE
CERTIFICATE OF CORRECTION

PATENT NO. : 7,185,401 B2
APPLICATION NO. : 11/016993
DATED : March 6, 2007
INVENTOR(S) : Ronald W. Ausen It is certified that error appears in the above-identified patent and that said Letters Patent is hereby corrected as shown below:

Column 28,
Line 1, In Claim 40, delete "front" and insert -- from --, therefor.
Line 5, In Claim 41, delete "front" and insert -- from --, therefor.
Line 6, In Claim 42, delete "hock" and insert -- hook --, therefor.
Line 18, In Claim 45, delete "polyethylenepolyethylene" and insert
-- polypropylene-polyethylene --, therefor.
Line 25, In Claim 47, delete "g2.5 cm." and insert -- g/2.5 cm --, therefor.

Signed and Sealed this

Seventh Day of August, 2007

JON W. DUDAS
*Director of the United States Patent and Trademark Office*